(12) United States Patent
Perego et al.

(10) Patent No.: US 11,596,520 B2
(45) Date of Patent: Mar. 7, 2023

(54) PERFECTED TOTAL SHOULDER PROSTHESIS

(71) Applicant: Permedica S.p.A., Merate (IT)

(72) Inventors: Marco Perego, Merate (IT); Federico Perego, Merate (IT); Hans Rudolf Paul Bloch, Dino (CH)

(*) Notice: Subject to any disclaimer, the term of this patent is extended or adjusted under 35 U.S.C. 154(b) by 142 days.

(21) Appl. No.: 16/640,481

(22) PCT Filed: Sep. 10, 2018

(86) PCT No.: PCT/IB2018/056880
§ 371 (c)(1),
(2) Date: Feb. 20, 2020

(87) PCT Pub. No.: WO2019/053576
PCT Pub. Date: Mar. 21, 2019

(65) Prior Publication Data
US 2020/0214846 A1 Jul. 9, 2020

(51) Int. Cl.
*A61F 2/40* (2006.01)
*A61F 2/30* (2006.01)

(52) U.S. Cl.
CPC .......... *A61F 2/4014* (2013.01); *A61F 2/4081* (2013.01); *A61F 2002/3093* (2013.01); *A61F 2002/30604* (2013.01); *A61F 2002/30616* (2013.01); *A61F 2002/30784* (2013.01); *A61F 2002/4051* (2013.01); *A61F 2002/4062* (2013.01); *A61F 2002/4085* (2013.01); *A61F 2310/00023* (2013.01); *A61F 2310/00179* (2013.01); *A61F 2310/00407* (2013.01)

(58) Field of Classification Search
CPC .... A61F 2/4014; A61F 2/4081; A61F 2/4059; A61F 2002/4011; A61F 2002/4018; A61F 2002/4037; A61F 2002/4044; A61F 2002/4051; A61F 2002/4062; A61F 2002/4081; A61F 2002/4085; A61F 2002/30616; A61F 2002/30784; A61F 2002/3093
See application file for complete search history.

(56) References Cited

U.S. PATENT DOCUMENTS

| | | | |
|---|---|---|---|
| 2005/0049709 A1 | 3/2005 | Tornier | |
| 2005/0177241 A1* | 8/2005 | Angibaud | A61F 2/4014 623/19.14 |
| 2006/0200249 A1* | 9/2006 | Beguin | A61F 2/4014 623/19.14 |
| 2011/0029089 A1* | 2/2011 | Giuliani | A61F 2/40 623/19.14 |
| 2012/0253467 A1* | 10/2012 | Frankie | A61F 2/4014 623/19.11 |
| 2013/0325133 A1* | 12/2013 | Viscardi | A61F 2/4003 623/19.14 |

FOREIGN PATENT DOCUMENTS

| | | |
|---|---|---|
| WO | 2007109800 | 9/2007 |
| WO | 2008015724 | 2/2008 |

* cited by examiner

*Primary Examiner* — Christopher D. Prone
(74) *Attorney, Agent, or Firm* — Themis Law

(57) ABSTRACT

A shoulder prosthesis includes a humeral portion and a scapular portion, each having an osseointegrable component and an articular component. The osseointegrable component in the humeral portion includes a humeral body produced as a semicircular asymmetrical cage having a proximal circular ring base facing the scapular portion and an eccentric distal cylindrical base in opposite position, which are connected by arms having one or more holes for favoring the growth of bone tissue and facilitating anchorage to the bone, the proximal circular ring base being configured to be interchangeably coupled with the articular component for an anatomical prosthesis or a concave insert for a reverse prosthesis. The osseointegrable component in the scapular portion includes a glenoid base-plate of asymmetric form for coupling to an articular component, such as a concave glenoid insert, for an anatomical prosthesis or a glenosphere for a reverse prosthesis.

15 Claims, 16 Drawing Sheets

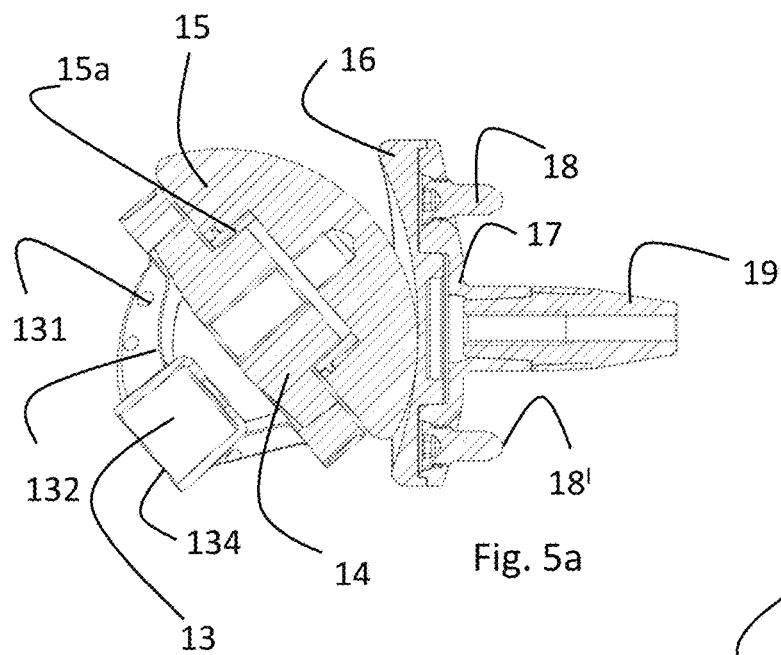
Fig. 5a
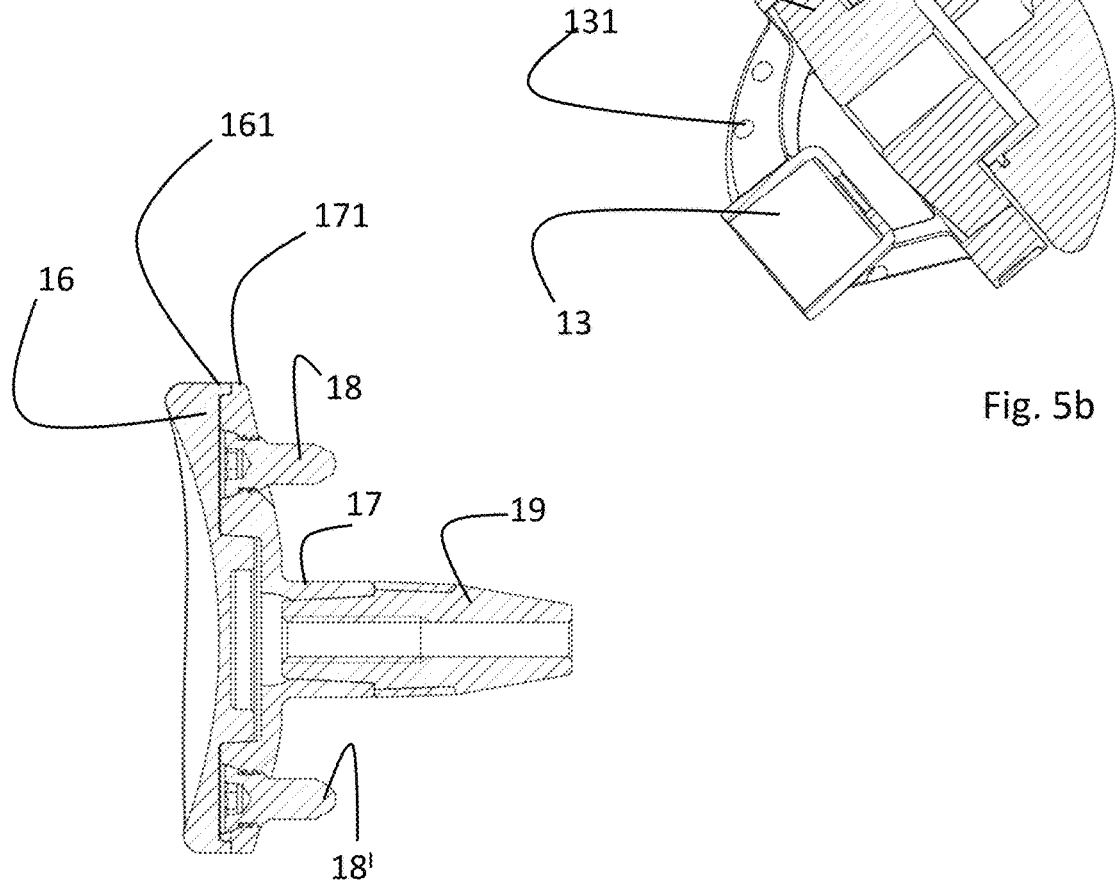
Fig. 5b
Fig. 5c

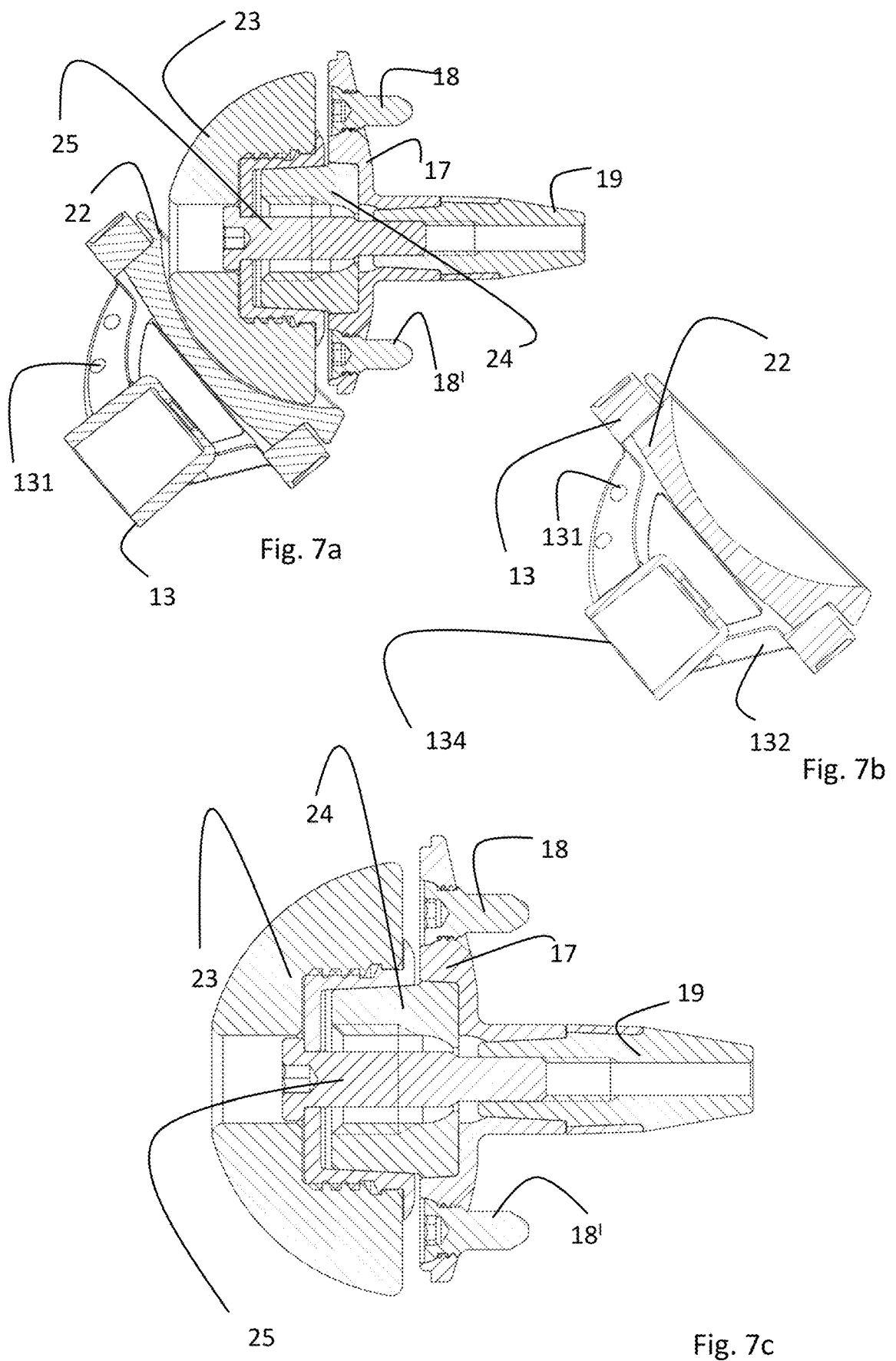

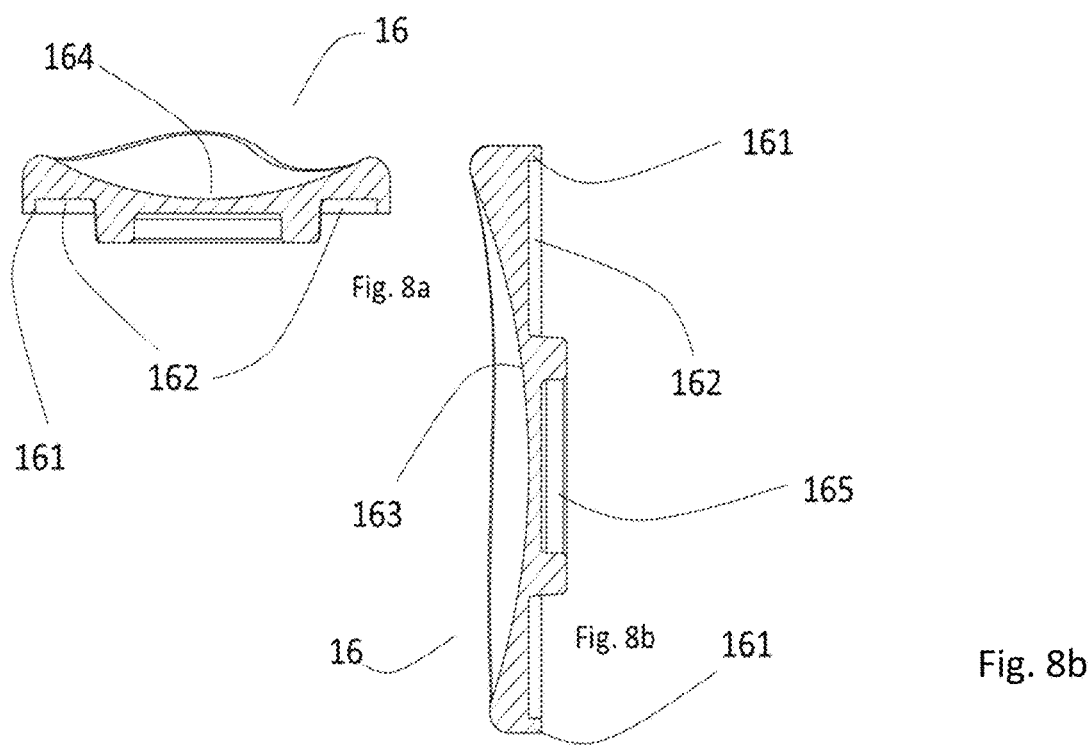
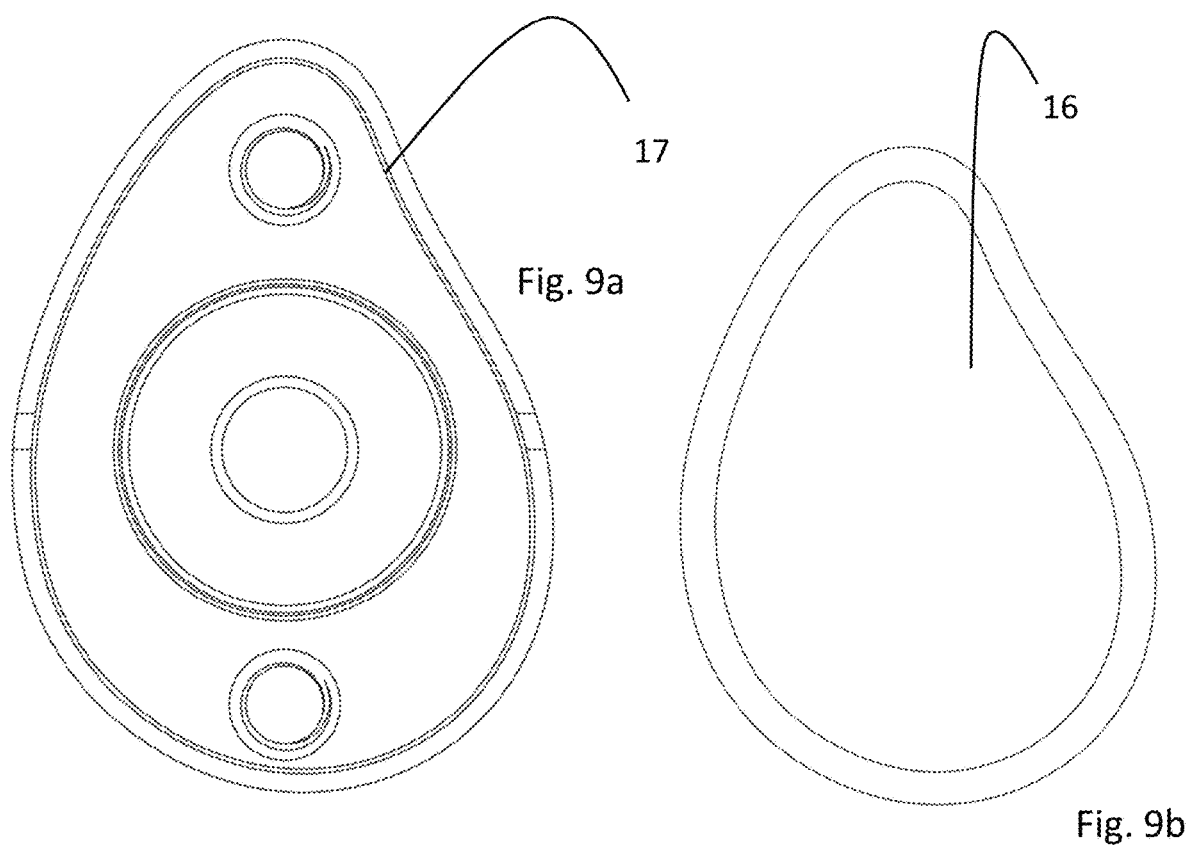

PERFECTED TOTAL SHOULDER PROSTHESIS

The present invention relates to a perfected total anatomical and reverse shoulder prosthesis.

As is well known to skilled persons in the field, shoulder arthroplasty is a reliable procedure for the treatment of severe pathologies of the glenohumeral joint for eliminating pain and restoring the functionality of the shoulder.

Articular prosthesis refers to an implantable device, including the implantable subsidiary components and materials, designed for exerting functions similar to those of a natural joint and which is put in connection with the corresponding bones.

Traditional shoulder prostheses with a humeral stem are commonly used in clinical practice.

The first shoulder prostheses were designed for treating cases of fractures of the humerus, for this reason the presence of the prosthetic humeral stem was therefore mandatory.

There are, however, frequent complications associated with the use of humeral stems. These complications include bone loss from the humerus, intra- and post-operative periprosthetic fractures, malpositioning of the humeral component, difficulty in treating deep infections involving the medullary cavity of the humerus and high intraoperative blood loss due to the opening of the medullary canal.

The most demanding part of the procedure is the anatomical reconstruction of the proximal humerus, especially in cases of post-traumatic malunion or in the case of dysplasia. Only a good reconstruction of the proximal humerus that respects the anatomy, allows good results to be obtained in terms of prosthetic stability, good articulation and longevity of the implant.

Intraoperative fractures of the humerus are often caused by excessively forced shoulder maneuvers, excessive milling of the medullary canal and incorrect insertion of the uncemented stem into the diaphysis. The result is often a long spiral fracture. The reported incidence of this complication is around 1.5%. A malpositioning of the humeral stem can in turn lead to a malpositioning of the humeral head.

Modular prosthetic designs of the humeral component have considerably improved the anatomical adaptability to the individual anatomy of the proximal humerus, in particular also especially in post-traumatic cases with severe deformity of the diaphyseal axis; a perfect anatomical reconstruction, however, is not always possible.

Postoperative complications relating to the humeral component mainly include fractures, especially in elderly patients with osteoporotic bone (between 1% and 3%) and mobilization of the stem (up to 5%).

Another potential risk is the removal of the stem in the event of a surgical revision. A vertical osteotomy is often necessary, particularly with uncemented stems or when a large layer of cement is present. This surgical procedure is associated with high morbidity, and the anchoring of a new prosthetic stem in the case of significant bone loss is difficult and often requires the use of a long revision stem.

The resurfacing of the humeral head was created to restore the normal anatomy of the shoulder with a minimal resection of the bone eliminating the complications relating to the stem and maintaining the "bone stock" for facilitating any possible future conversion revisions into a total conventional shoulder prosthesis.

Resurfacing arthroplasty, however, has also shown numerous limitations. It is not suitable, in fact, in cases of severe deformity of the proximal humerus, post-traumatic malunion or extensive necrosis for more than 35% of the humeral head.

It can be associated with a varus/valgus malpositioning of the humeral component, with a consequent increased wear of the glenoid, and can generate excessive tensioning in the soft tissues, with a consequent increase in muscle tension and a reduction in the "range of motion".

Furthermore, the exposure of the glenoid is difficult when the humeral head remains in situ, thus requiring an extensive peripheral release of the soft parts.

Pursuing the objective of reducing the complications relating to the stem and eliminating the mobilization of the humeral component while maintaining the advantages of a third generation of shoulder prostheses, in 2004 a group of French surgeons introduced the first stemless humeral prosthesis (TESS®, Biomet Inc., Warsaw, Ind.).

The aim of a stemless humeral prosthesis is to reconstruct the anatomy of the humeral head without the need for using a stem, with an automatic centering, through a simple and reproducible surgical technique, maintaining the bone stock of the humerus and, at the same time, allowing an adequate exposure of the glenoid.

Numerous recent studies have shown excellent results following the use of this stemless prosthesis, also comparing them directly with traditional stemmed prostheses.

The decision to resort to a prosthetic glenoid replacement remains debatable. This uncertainty is based on the potential negative effects of glenoid wear with the partial shoulder prosthesis that contrasts with the risks relating to the mobilization and failure of a glenoid prosthetic component.

Improved clinical results, however, in terms of pain relief and joint functionality are proven with the use of total shoulder replacement compared to the use of endoprosthesis. Patients with arthritis treated with endoprosthesis often remain symptomatic even in the long term.

In general, the long-term mobilization of the glenoid component does not appear to be an indication in favour of endoprosthesis compared to total arthroplasty. Furthermore, another aspect to the detriment of endoprosthesis is that a revision for converting an endoprosthesis to a total arthroplasty can be made difficult by the erosion of the glenoid.

In shoulder arthroplasty, the choice of the correct prosthetic device is effected in certain cases during surgery. It is therefore preferable to use a prosthetic system that provides the surgeon with the possibility of an intraoperative choice of different prosthetic configurations (stemmed, stemless, anatomic, reverse), depending on the anatomy of the proximal humerus, the quality of the bone, the state of the glenoid and the state of the rotator cuff.

Even with careful preoperative planning with bone densitometry tests, it is possible to find intraoperatively a bone quality not corresponding to that evaluated preoperatively, so that the possibility must be provided of intraoperatively changing from a stemless system to a stemmed system.

As the stemless humeral component (called "core" in technical jargon) is implanted in the metaphyseal bone with the anatomical CCD angle of the patient, the fixing of the humeral stem must absolutely consider the offset.

Different sizes of the core, together with an asymmetrical arrangement of the anchorage branches in the metaphyseal bone, are basic for an uncemented stemless humeral component. In the case of immediate conversion from a stemless to stemmed implant during surgery, different offsets can guarantee a correct coupling between the core and the stem without modifying the joint geometry but re-establishing the articular parameters planned before surgery.

The prosthesis according to the present invention has been conceived and developed maintaining the concept of modularity on the glenoid side and on the humeral side in order to provide solutions for a wide spectrum of indications for shoulder arthroplasty.

This prosthesis allows a total anatomical shoulder arthroplasty to be performed and to convert it to reverse using the same stemless humeral core that does not need to be replaced if it is stable and osseointegrated in the case of revision.

The aseptic loosening of the glenoid component is still the most common complication in total anatomical shoulder arthroplasty. The overall incidence of glenoid mobilization reaches up to 14% in total shoulder arthroplasty.

The mobilization of the glenoid component in the total prosthesis is a phenomenon considered as being the result of multiple factors, among which an eccentric load (caused by a deficiency or failure of the rotator cuff or other instability of the soft tissues), polyethylene wear osteolysis, an inadequate cementation technique, malpositioning of the implant or over-stuffing of the joint.

Shoulder prostheses of the known type are described, for example, in patents: WO2007/109800, FR 2652498, EP 1787603, WO 2015/001525A1 which corresponds to IT1418610.

On page 2 of WO2015/001525A1 the following can be read:

"Starting from this known technique, the objective of the present invention is to provide a prosthesis for reconstructing the shoulder joint which is alternative to those known, particularly efficient and capable of achieving the following results:

Reducing the risks of detachment at the glenoid;

Eliminating faults or breakages of the front portion of the glenoid joint; and

Facilitating the transition from the anatomical configuration to the reverse configuration.

In general, the present invention achieves the results indicated above by inverting, in an absolutely innovative manner and contradicting the standard currently known, the tribological characteristics of the coupling at the base of the prosthesis for the reconstruction of the shoulder joint.

In particular, it is provided that the front portion of the glenoid joint be made of a metallic material and the corresponding portion of the humerus is plastic material.

The fixing portions to both the glenoid and the humerus are made of a metal material of the "cementless" type, i.e. fixed in place by means of threaded elements, and are configured to removably receive the relative articulation portions. In this way, it is much easier to pass from an anatomical configuration to a reverse configuration."

(Italian translation from IT1418610)

This objective is achieved by producing a shoulder prosthesis comprising:

a glenoid prosthesis comprising a fixing support to the glenoid and a glenoid articulation element;

a humeral prosthesis comprising a fixing support to the humerus and an articulation element of the humerus.

Said articulation elements of the glenoid and humerus are shaped so as to create a spherical-type coupling for the artificial reconstruction of the shoulder joint, the glenoid articulation element having a concave surface and the element of articulation of the humerus being hemispherical-shaped.

The articulation element of the humerus is made of a plastic material (polyethylene) whereas the articulation element of the glenoid is made of a metallic material (cobalt-chromium alloy).

A shoulder prosthesis produced in this way does not guarantee a lasting integration of the prosthesis to the bone structure of the shoulder, in particular to the humerus.

Furthermore, the spherical coupling between the articulation elements leads to considerable wear osteolysis of the polyethylene.

An anatomical prosthesis is also described in patent US2005/0049709 wherein the glenoidal component comprises a metal body whose inner surface is suitable for being immobilized in the glenoid cavity of the shoulder and the outer surface has a concave articulation surface suitable for cooperating with the humeral component.

The humeral component 4 comprises a stem anchored to the medullary cavity and a hemispherical head which, at least in its peripheral part, is made of polyethylene, in particular high-density polyethylene (HDPE).

US patent 2012/0253467 describes both an anatomic prosthesis and a reverse prosthesis.

The glenoid component 300 (700 in the reverse prosthesis) is made of ceramic, metal or other biocompatible material whereas the humeral component 500 (800 in the reverse prosthesis) is made of ceramic, polyethylene or another biocompatible material.

The document also describes a prosthesis provided with a stem and does not describe components of the prosthesis that can be used for implanting prostheses with or without a stem, depending on the patient's needs.

The document WO 2007/109800 describes a reverse shoulder prosthesis that can be transformed into an anatomical prosthesis leaving the stem inserted in the bone. The document does not describe a stemless prosthesis.

The document WO 2008/015724 describes a modular shoulder prosthesis provided with a stem suitable for passing from direct to a reverse configuration.

The prosthesis body 16 comprises supporting flaps 40 which define an angle with each other so as to receive in abutment the tuberosities of the humerus 20.

The supporting flaps 40 have holes 44 to allow the passage of a thread for the re-sewing of the tuberosities 20.

An engagement portion in the form of a cup suitable for interacting with a glenosphere associated with a corresponding glenoid, is associated with the prosthetic body, with a coupling of the male female type.

As shown in FIG. 35, the component 16 engages directly on the stem inserted in the humerus.

The objective of the present invention is to overcome the above-mentioned drawbacks, and those of the known art in general, by producing a total shoulder prosthesis capable of combining the advantages of the known art and a: the same time eliminating the drawbacks.

According to the present invention, this objective is achieved by producing a shoulder prosthesis having the characteristics set forth in claim 1 and the sub-claims.

According to the present invention, the modular system claimed with a humeral body having a surface at least partly trabecular, as described hereunder, allows a rapid and easy passage from a stemless prosthesis to a stemmed prosthesis and from an anatomical prosthesis to a reverse prosthesis.

The trabecular surface allows an excellent and high bone re-growth inside the pores and a fast osseointegration of the components for an optimal secondary stability.

The trabecular structure of the surfaces of the components object of the present invention, has a high friction coefficient with the bone for allowing a high initial press-fit of the implant.

The characteristic asymmetric pear shape of the anatomical glenoid insert of the present invention allows an optimal articular surface to be obtained.

According to the present invention, the combination of the inversion of the materials of the modular articular components with the non-spherical geometry of the prosthetic humeral head improves the prosthetic stability and decreases the wear of the polyethylene in the anatomical prosthesis.

As metal implants can be produced with thinner thicknesses with respect to polyethylene components, the risk of over-stuffing the reconstruction of the glenohumeral joint in total anatomical arthroplasty is considerably reduced by using a metal-back (basal plate or base-plate) with trabecular titanium for anchorage with the glenoid bone and covered with a thin metal insert.

According to the present invention, in the case of the need to convert from a total anatomical prosthesis to a total reverse prosthesis, the metallic glenoid insert can be disassembled from the metal-back, leaving the metal-back (basal plate or base-plate) in situ and substituting the insert with a polyethylene glenosphere. On the humeral side, in the case of conversion from anatomical to reverse, the humeral polyethylene head can be replaced by a metal reverse prosthetic insert, available in different thicknesses.

Anatomical glenoid implants with an uncemented metal-back as produced according to the present invention have the advantage of a simpler surgical revision in the case of conversion into a reverse prosthesis due to a failure of the cuff, as the metal back can be left, if stable and osseointegrated, replacing only the polyethylene insert.

The longevity of metal-back implants can be increased by improving the mechanical anchorage of the metal-back with the glenoid bone in the anatomical prosthesis, thus respecting the radius of anterior-posterior and superior-inferior curvature of the glenoid.

The current use of an imperfect radial coupling of the spherical humeral head in order to allow a translation motion is a compromise that reduces the contact area with the glenoid component which can cause polyethylene wear, joint instability and prevents correct articular kinematics.

The use of a non-spherical humeral head, in articular coupling with a two-radius curvature glenoid surface, reduces polyethylene wear in the glenoid and improves joint stability by better reproducing the physiological kinematics between the head of the humerus and the scapular glenoid.

A non-spherical elliptical prosthetic head replicates more accurately the anatomical shape of the patient's humeral head, the range of motion in rotation, the kinematics of the glenohumeral joint compared to the models of spherical prosthetic heads available on the market.

A biomechanical study has shown that a non-spherical humeral prosthetic head increases the stability of the glenohumeral joint.

According to the present invention, the elliptical shape of the base of the humeral head extends with an increasing size of the anatomical humeral head.

The most common complication in total reverse shoulder prosthesis is the scapular notching, osteolysis of the lower lateral edge of the scapula caused by the conflict between the scapula and the polyethylene humeral insert. In addition to being associated with a greater risk of mobilization of the glenoid component, scapular notching is also associated with inferior clinical results.

According to the present invention, in order to avoid wear from scapular impingement of the humeral insert, a metal humeral insert is provided, articulated against a polyethylene glenosphere.

In the case of conversion from stemless to stemmed prostheses, such as, for example, in cases of trauma after total anatomical or reverse prosthesis, a metaphyseal humeral component with variable offsets gives the possibility of connecting a well-osseointegrated humeral core to a humeral stem having a variable length, from short to long up to 215 mm for revision cases.

The prosthesis object of the present invention combines all the advantages of a stemless prosthetic system of a first implant with the possibility of broadening the indications to a procedure that requires the use of a humeral stem with an easy conversion from anatomical prosthesis to reverse, using a single prosthetic system and without having to replace the osseointegrable components but only the modular articular components.

The structural and functional characteristics of the invention, and its advantages with respect to the known art, can be clearly understood from the following description, referring to the attached drawings, which illustrate non-limiting embodiment examples of the invention itself.

In the drawings:

FIGS. 5a, 5b, 5c are sections of the prosthesis of FIG. 4;

FIGS. 7a, 7b, 7c are sections of the prosthesis of FIG. 6;

FIG. 8a is an anterior-posterior section of the glenoid insert;

FIG. 8b is an upper-lower section of the glenoid insert;

FIG. 9a is a front view of the glenoid base-plate;

FIG. 9b is a front view of the concave glenoid insert;

The prosthesis according to the present invention allows, thanks to its modularity:

an anatomical configuration (FIG. 2, FIG. 4, FIGS. 5a, 5b, 5c) and a reverse configuration (FIG. 3, FIG. 6, FIGS. 7a, 7b, 7c);

a stemless configuration (FIG. 4, FIGS. 5a, 5b, 5c, FIG. 6, FIGS. 7a, 7b, 7c) and a stemmed configuration (FIG. 2, FIG. 3) of the humeral portion;

a first plant configuration and a revision configuration.

Thanks to the present invention, it is possible to pass from one configuration to another without having to change prostheses 10 but only by adding/substituting the appropriate components within the same prosthesis 10.

With reference to the figures of the drawings, a total shoulder prosthesis with a stem (FIG. 1) or without a stem, produced according to the present invention, is generally indicated with 10 and is modular or structurally composed of the following components operationally inter-coupled.

Figure 20:
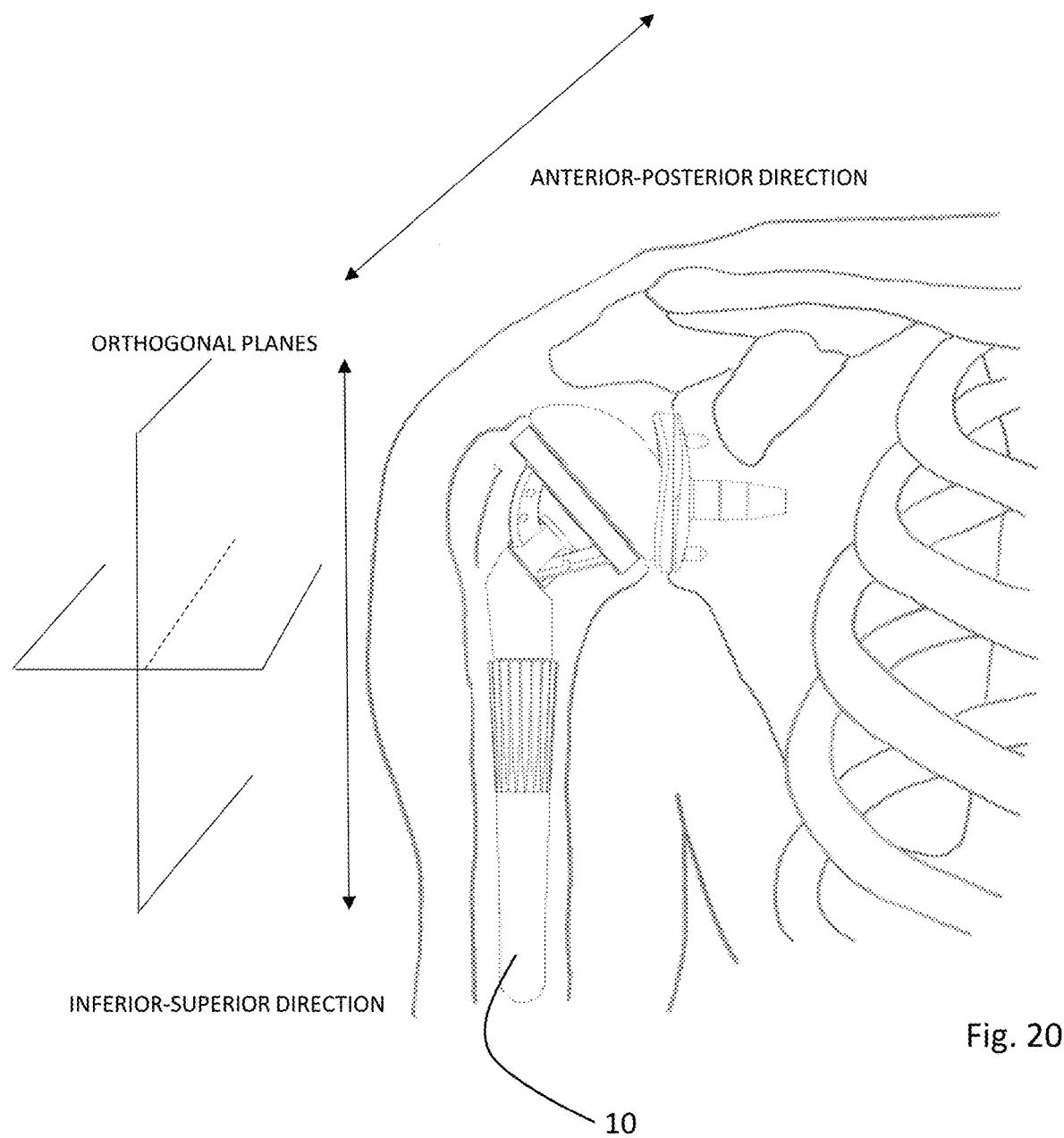
FIG. 20 is a schematic perspective view illustrating the total shoulder prosthesis of the invention implanted in the human body.

FIG. 20 shows the implanted prosthesis 10 with the anterior-posterior and inferior-superior directions highlighted, with respect to a patient in an upright position.

The total prosthesis according to the present invention comprises a humeral portion and a scapular portion, each portion being provided with at least one osseointegrable component and articular component.

The humeral portion of the prosthesis 10 can comprise one or more of the following elements:

a) a humeral body 13, or so-called "humeral core", which allows the passage intraoperatively and with the same prosthetic system from a stemless humeral configuration to a stemmed configuration and from an anatomical to an reverse configuration.

The humeral body 13 is made of a metallic material.

The humeral body 13 can be made of titanium alloy Ti6Al4V in powder form (according to the standard ASTM F3001).

The body 13 is produced in the form of a semispherical asymmetric cage with multiple arms 132 and having a proximal circular ring base 133 suitable for being interchangeably coupled with the articular component such as a humeral head 15 for an anatomical prosthesis or a concave insert 22 for a reverse prosthesis.

In particular, the body 13 is produced as a semispherical asymmetric cage.

As illustrated in the figures, said humeral body 13 produced as a semispherical asymmetric cage is in the form of a pyramid having as its base the proximal circular ring base 133 and as the apex, to which it is connectable, through a connector 12 (as described hereunder) a stem 11, a base 134 provided opposite and eccentric with respect to said proximal base 133.

Said base 134 has a cylindrical form.

In the embodiments illustrated, said base 134 has a hollow cylindrical form so as to house in its interior an end 121 of the connector 12.

The coupling between said distal base 134 and connector 12 is of the morse cone type.

As can be seen in FIG. 20, in a mounted condition of the prosthesis 10, the proximal circular ring base 133 faces the scapular portion and the distal base 134, opposite, is inserted into the humerus.

The proximal circular ring base 133 and the distal base 134 are connected to each other by arms 132.

As shown in the figures therefore, said humeral body 13 produced as a semispherical asymmetric cage is hollow inside and with empty spaces between adjacent arms 132.

According to an embodiment illustrated, said humeral body 13 is provided with four arms 132.

Advantageously, of the arms 132 has pass-through holes 131 for favouring the growth of new bone tissue inside and facilitating the anchorage of the body 13 to the bone.

Figure 13:
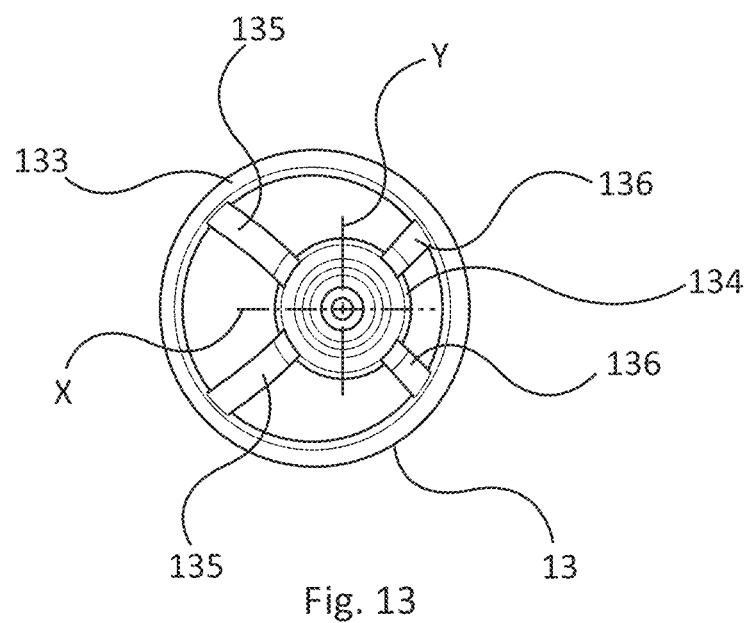
FIG. 13 illustrates the position of the arms of the humeral body.

As illustrated in FIG. 13, according to a preferred embodiment, the humeral body 13 has four arms 132 positioned asymmetrically with respect to each other, connecting the circular ring of the proximal base 133 to the distal base 134 of the humeral body 13, thus forming a hemispherical cage.

The four arms 132 are asymmetric with respect to an axis Y in an anterior-posterior direction passing through the centre of the distal base 134.

This asymmetry is due to the eccentricity of the distal base 134 with respect to the proximal base 133 on the transverse plane which involves two arms having a greater size and length 135 on the lateral side of the distal base 134 with respect to the two arms having a smaller size and length 136 positioned on the medial side of the distal base 134 according to a direction described by an axis X perpendicular to Y.

These four arms give a greater rotational stability of the humeral body (with respect, for example, to a body with three flaps such as that described in the prior art), greater support on the metaphyseal humeral bone and therefore greater stability against a downward distal migration (sinking) of the humeral body 13.

The two major lateral arms 135 are inserted in the bone portion of the major tubercle. The two minor medial arms 136 are inserted in the bone portion of the humeral neck.

Figure 10A:
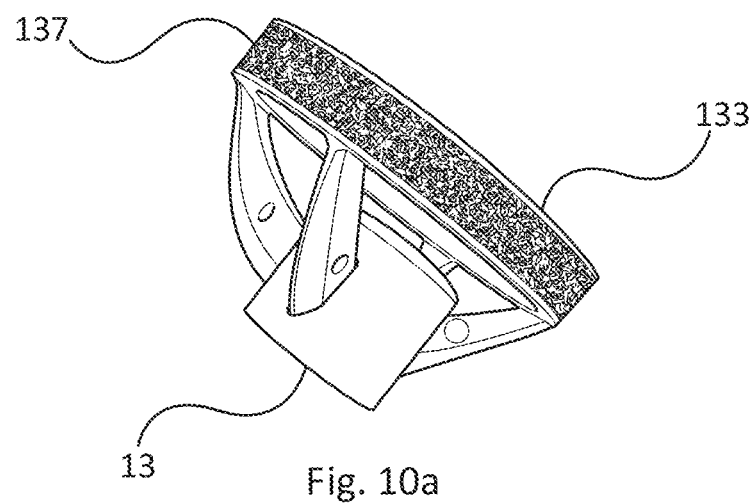
FIGS. 10a and 10b illustrate the trabecular surface of the humeral body.
Figure 10B:
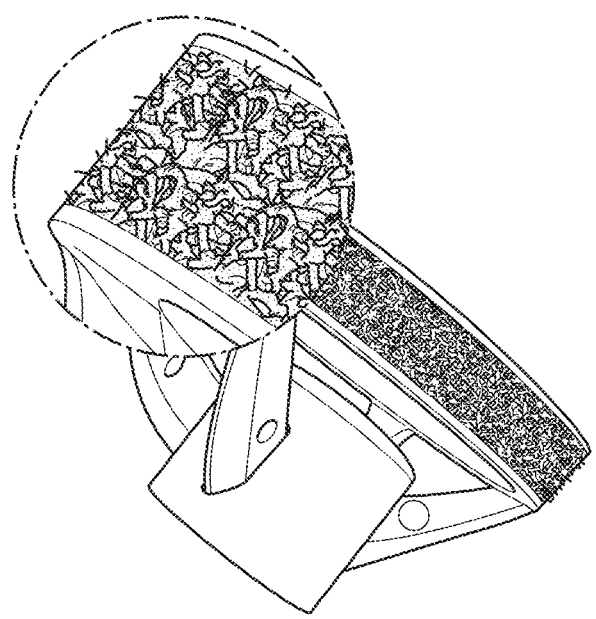
Figure 11:
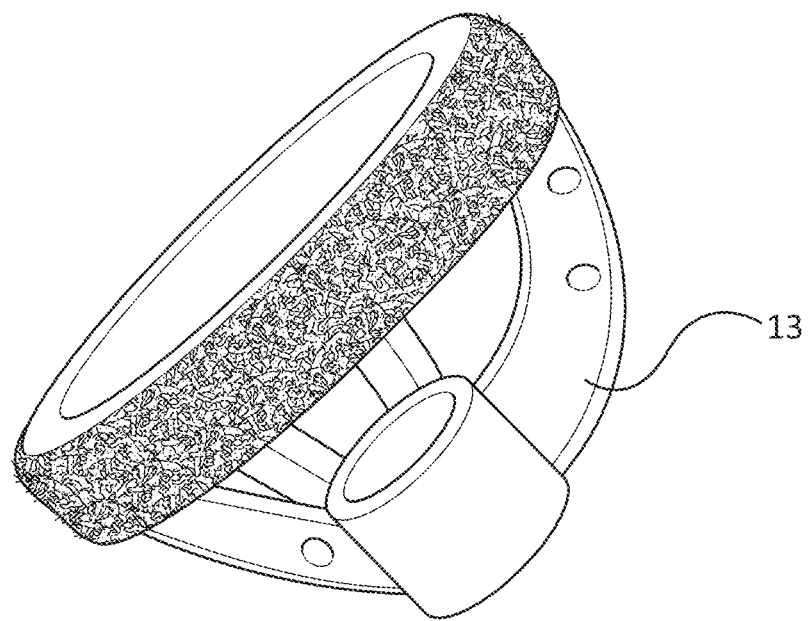
FIG. 11 illustrates an embodiment of the humeral body having a trabecular surface on arms, ring base and distal base.

As illustrated in FIGS. 10a, 11 and in the detail illustrated in FIG. 10b, the humeral body 13 has, at least on the outer annular side 137 of the proximal circular ring base 133, an irregularly isotropically oriented trabecular structure, highly porous to facilitate anchorage by the initial press-fit and its osseointegrability and osseoinductivity.

Said annular outer side 137 has, in fact, a highly porous isotropic metal structure, with interconnected trabeculae and irregularly and randomly arranged in space in order to favour the initial anchorage of the humeral body 13 (which in one of the embodiments can be stemless) by pressure interlocking with the bone of the humeral metaphysis and to favour the secondary biological anchorage through its characteristics of osseoinductivity and osseointegrability.

Figure 12:
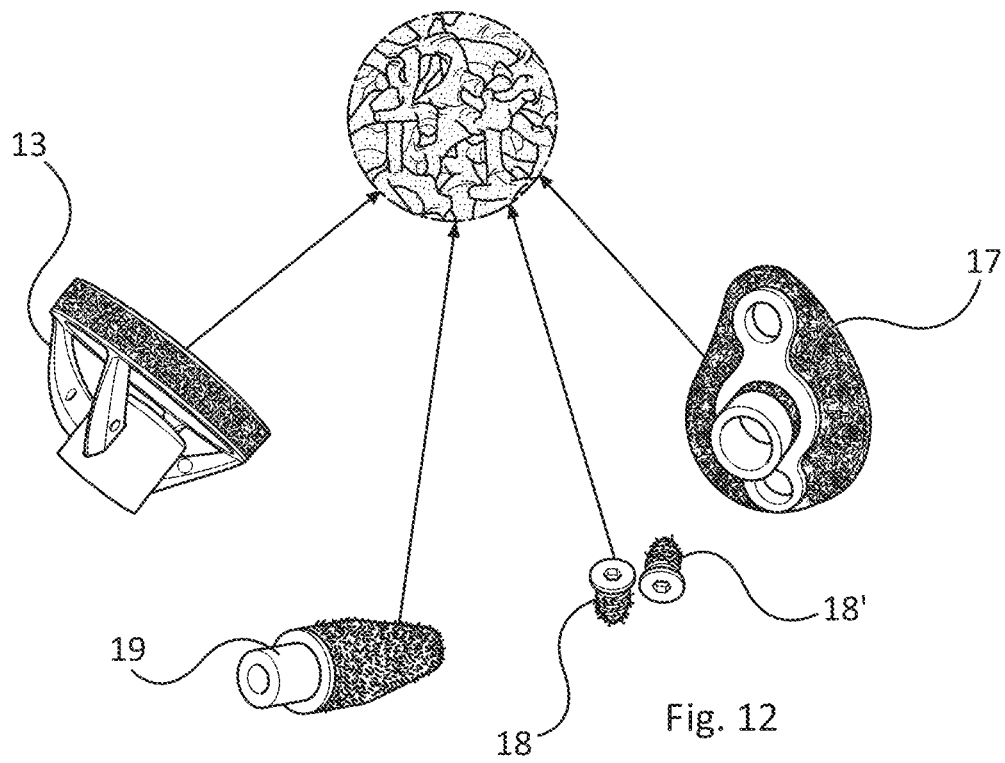
FIG. 12 illustrates various components of the prosthesis object of the present invention with a trabecular surface.

As illustrated in FIGS. 11 and 12, other parts of the humeral body 13 or other components of the prosthesis, both in the humeral and scapular portion, can have a highly porous, isotropic metallic structure, with trabeculae interconnected and arranged irregularly and randomly in space.

The humeral body 13, object of the present invention, is osseointegrable, osseoinductive and modular, i.e. it has a cement-free fixation to the metaphyseal humerus or can be assembled to a humeral stem by a metaphyseal humeral connector 12 (described hereunder) for a distal fixation and no longer metaphyseal to the bone of the limb and is also suitable for housing an interchangeable articular component to effect an anatomic or inverse shoulder prosthesis.

b) a humeral stem 11, obviously provided in the stemmed prosthetic configuration.

Said humeral stem 11 can be available in the first implant configuration and in the revision configuration, with a cementless or cemented fastening mode.

The humeral stem 11 can have various diameters and lengths.

The humeral stem 11 can be made of titanium alloy or titanium alloy and hydroxyapatite.

It can be made, for example, of titanium alloy Ti6Al4V (according to the standard ISO 5832/3) or titanium alloy according to the standard ISO 5832/3 and coated with hydroxyapatite according to the standard ISO 13779;

c) a metaphyseal humeral connector 12 that allows the passage of the prosthetic configuration without a stem (stemless) to the configuration with a stem (stemmed).

It is the component through which the humeral stem 11 is fixed to the humeral body 13 ("humeral core"), in particular said connector 12 is coupled, at one of its ends 121, to the distal base 134 of the humeral body 13 like a cage, provided opposite and eccentric to the proximal base 133.

This component 12 is available in different offsets and CCD angles.

Figure 14:
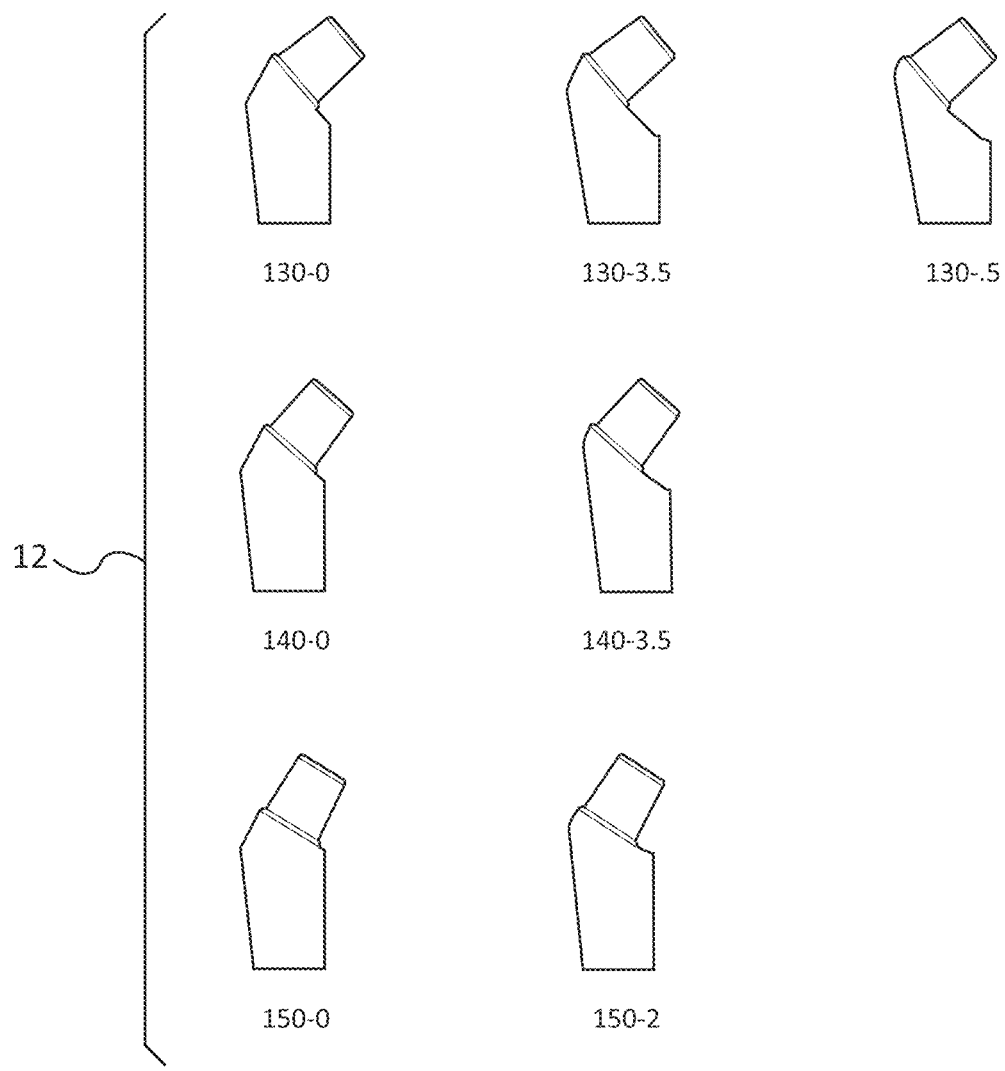
FIG. 14 illustrates metaphyseal humeral connectors with various offsets and various CCD tilt angles.
Figures 15A, 15B:
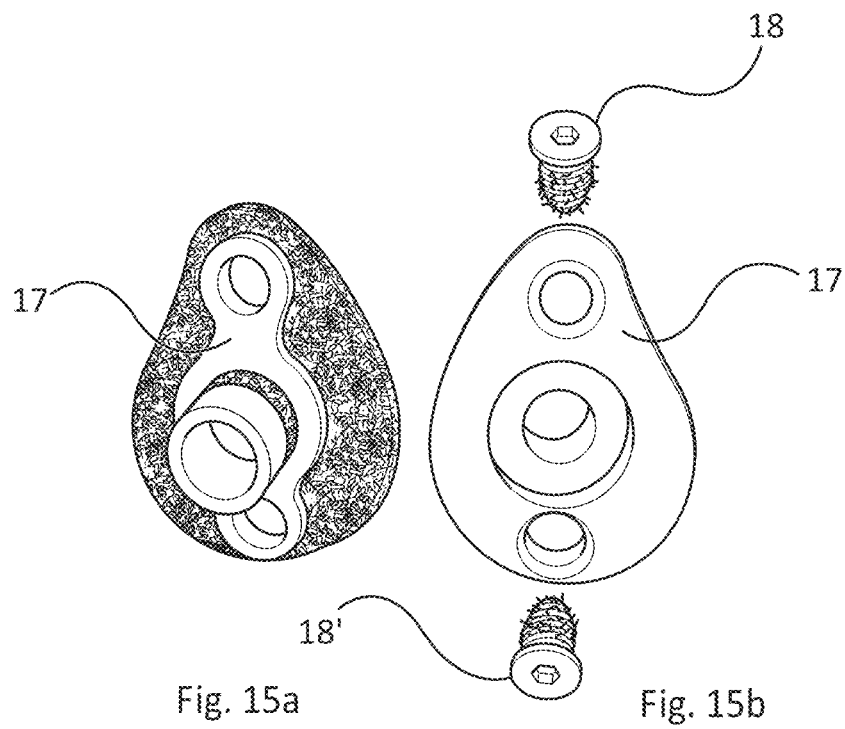
FIGS. 15a and 15b illustrate a front and rear view (i.e. that positioned in contact with the bone in a mounted condition of the prosthesis on the glenoid) of the glenoid base-plate with a trabecular structure.
Figures 16A, 16B:
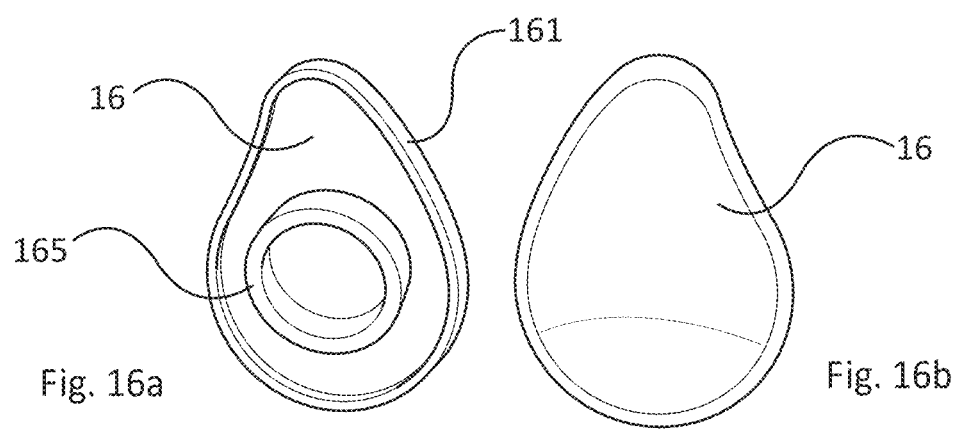
FIGS. 16a and 16b illustrate a front and rear view (i.e. that positioned in contact with the base-plate in a mounted condition of the prosthesis on the glenoid) of the anatomical glenoid insert with the characteristic form object of the present invention.

As illustrated in FIG. 14, the metaphyseal humeral connector 12 can have various offsets and various CCD tilt angles for restoring the position of the stemless humeral component 13 with respect to the humerus when using a distal fixation through a humeral stem 11.

The metaphyseal humeral component 12 can be made of titanium alloy Ti6Al4V powder (according to the standard ASTM F3001);

d) a humeral head 15, which forms the articular humeral component in the anatomic prosthetic configuration (conventional).

Advantageously, it has an articulation surface, with the concave glenoid insert 16 illustrated in FIG. 9b, convex with an elliptical cross-section with two diameters (anterior-posterior diameter DA-P and an inferior-upper diameter DI-S).

Figure 18:
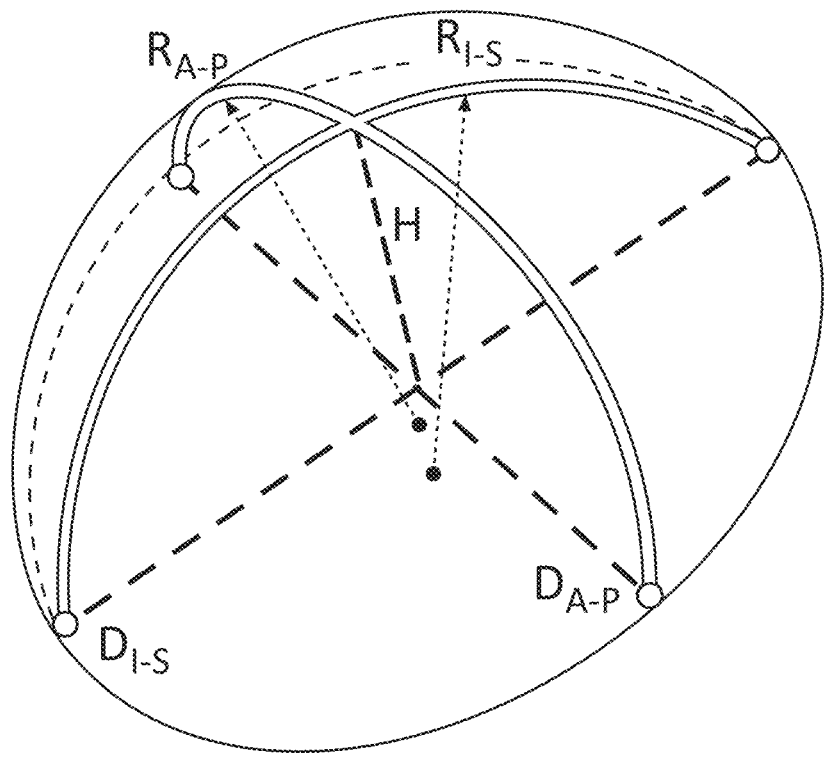
FIG. 18 illustrates the anatomical humeral head with an ellipsoidal geometry.

As illustrated in FIG. 18, the humeral head 15 has an elliptical base with two axes and an ellipsoidal convex articular surface, characterized in each size by two curvature profiles described in two orthogonal planes frontal and transversal and described by two radiuses, one in the anterior-posterior direction (RA-P) (transverse plane) and one in an inferior-superior direction (RI-S) (coronal plane).

The articular surfaces of the two modular anatomical articular components of the humeral head 15 and the glenoid insert 16 coupled together, replicating the radial mismatch between the cartilage surfaces of the glenoid and the anatomical humeral head, create a difference in radius of curvature, different at each considered point of contact between the surfaces.

Figure 19:
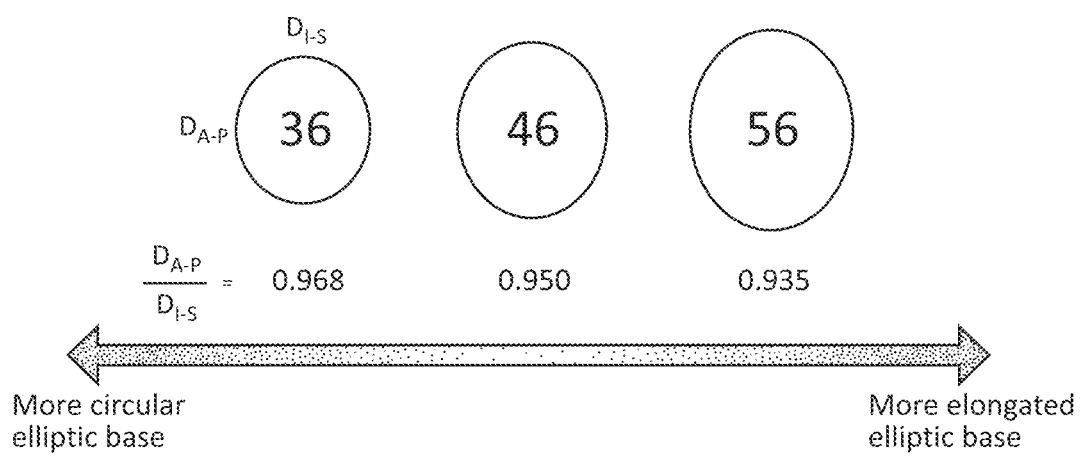
FIG. 19 illustrates the ratio between the anterior-posterior diameter and the inferior-posterior diameter of the anatomical humeral head in the various sizes.

The humeral head 15 can obviously be of different sizes. FIG. 19 shows various sizes of the humeral head 15, non-spherical, with a base having an elliptical section.

According to the present invention, the anatomical humeral head 15 therefore has the following characteristics:
a non-spherical head with an ellipsoidal geometry,
a base with an elliptical section with a major axis and a minor axis,
an articular surface with two curvature profiles described by two different medium radiuses,
coupled by means of a morse cone with an adapter 14 for connection to the humeral body 13.

This humeral head in the anatomical prosthesis is made of plastic material.

According to the present invention, it is made, in the anatomical prosthesis, of Ultra-High-Molecular-Weight Polyethylene.

The anatomical humeral head 15 can be made, for example, of UHMWPE or UHMWPE stabilized with vitamin E.

Said humeral head 15 is coupled with said proximal base 133 of the humeral body 13 through:
an adapter for a humeral head 14 for the assembly of an anatomical humeral head 15 on the humeral body (humeral core) 13. It can be made of Ti6Al4V titanium alloy (ISO 5832/3);
a ring for a morse cone of the humeral head 15a which is a component pre-assembled to the female morse cone 151 of the humeral head 15. It can be made of titanium alloy, for example Ti6Al4V (ISO 5832/3).

The scapular portion of the prosthesis 10 can comprise one or more of the following elements:
a) a concave glenoid insert 16, which forms the glenoid articular component in the anatomical prosthetic configuration (conventional).

Figures 17A, 17B, 17C:
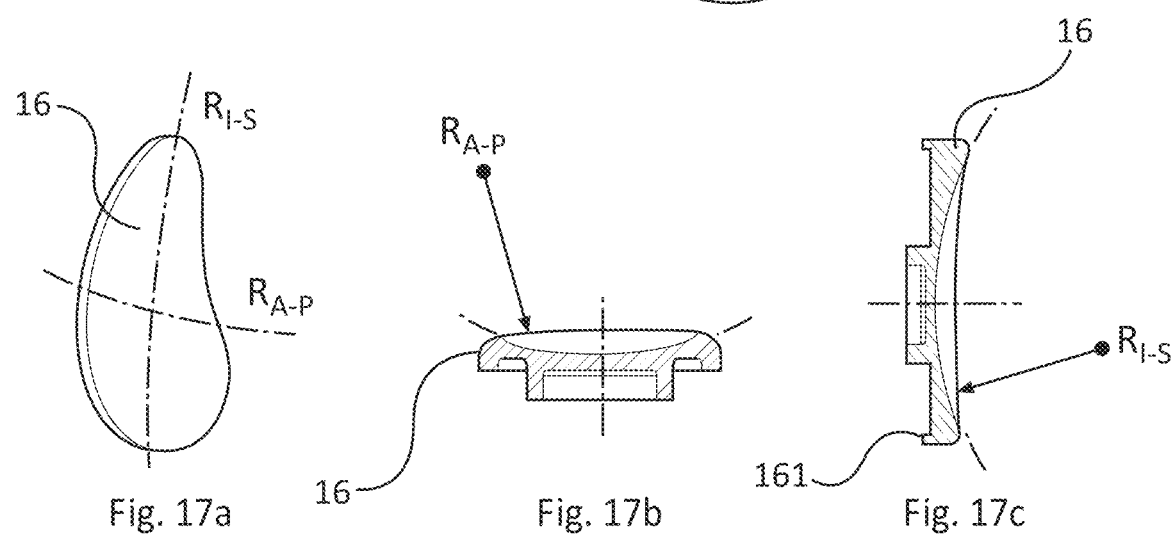
FIGS. 17a-17c illustrate the anterior-posterior radius RA-P (transverse plane) and the inferior-superior radius RI-S (coronal plane) of the anatomical glenoid insert.

As illustrated in FIG. 9b, it has an asymmetrical pear shape, i.e. it is asymmetrical with respect to both an anterior-posterior plane and to an inferior-superior plane, said planes being orthogonal to each other, as shown in FIG. 17a, 20, considering the prosthesis implanted on a patient in a vertical position.

Advantageously it has an anatomical asymmetric form with a concave articular surface having an ellipsoidal form described in each size by two curvature profiles described in two orthogonal planes, frontal and transversal, and described by two radiuses, in particular a curvature profile 163 described in the transverse plane in an inferior-superior direction by a first radius (RI-S) and a second curvature profile 164, different from 163, described in the transversal plane in the anterior-posterior direction (orthogonal to said transversal plane in an inferior-superior direction) by a second radius (RA-P) (FIGS. 8a, 8b and 9b, 16a, 16b, 17a, 17b, 17c).

It can obviously have different sizes for both the right side and the left side.

The two radiuses on the glenoid side and an elliptical form of the head allow the stability and the articulation of the glenohumeral joint to be improved.

According to the present invention, it is produced, in the anatomical prosthesis, in a metallic material.

The fact of producing the concave glenoid insert 16 in metal allows the thicknesses of the component to be reduced, thus allowing the anatomy of the glenoid to be respected, maintaining the original articular line, improving the articulation of the shoulder, reducing the risk of overstuffing (stiff and painful shoulder by compression of the soft tissues).

Furthermore, producing it in TiNbN-coated metal makes it much lighter with respect, for example, to a Chromium-Cobalt alloy and makes it tribologically compatible in articulation with the humeral head in UHMWPE. In particular it can be made of TiNbN-coated titanium alloy.

According to an embodiment, it is made of titanium alloy such as for example Ti6Al4V (ISO 5832/3) and coated via PVD (Physical Vapour Deposition) in TiNbN; b) a glenoid basal plate (so-called base-plate) 17 (FIG. 9a) which forms the anchoring component to the glenoid bone over which it is coupled or the concave glenoid insert 16 in the anatomical prosthesis configuration (conventional) or the glenosphere 23 in the reverse prosthesis configuration.

Advantageously it has an anatomical asymmetric form congruent to the form of the concave glenoid insert 16 (FIGS. 15a-15b and 16a-16b).

It can obviously have different sizes for both the right side and the left side.

According to the present invention, the glenoid base-plate 17 is produced with the SLM (Selective Laser Melting) technology characterized on the glenoid side by a trabecular structure (FIG. 15a), highly porous, in titanium alloy (Traser®), or it is produced with the SLM technology with hydroxyapatite plasma spray coating on the glenoid side without trabecular titanium (Traser®).

The trabecular surface of one or more components of the shoulder object of the present invention, allows an excellent and high bone re-growth within the pores and a rapid osseointegration of the component for an optimal secondary stability.

The trabecular structure, such as, for example, Traser®, has a high friction coefficient with the bone to allow a high initial press-fit of the implant.

One or more of the components are produced with the SLM technology.

The solid and trabecular parts of one or more of the components are produced in a single process without discontinuity or coatings.

The glenoid base-plate 17 is made of a metallic material.

The glenoid base-plate 17 can be made of titanium alloy powder such as for example Ti6Al4V (ASTM F3001/14).

The glenoid base-plate 17 characterized by a highly porous metallic structure, with a trabeculation similar to that of cancellous bone, allows an optimal bone re-growth within its pores and a rapid osseointegration, thus ensuring a stable anchorage of the implant of the scapular glenoid guaranteed by osseointegration of the base-plate 17.

Said concave glenoid insert 16 is coupled with said glenoid base-plate 17 by a morse cone coupling and interlocking.

The assembly between the modular anatomical glenoid insert 16 and the glenoid base-plate 17 is effected by means of a morse cone 165 and the antirotational blocking by means of the outer edge 161, as a peripheral flange, of the glenoid insert 16 which surrounds the step edge 171 of the glenoid base-plate 17 which is thus located, once assembled with the glenoid insert, inside the recess 162 of the glenoid insert 16 produced on the scapular side (i.e. on the side of the insert 16 facing the scapula in a mounted condition of the prosthesis) (FIGS. 8a and 8b), thus blocking it against rotations (anti-rotational blockage). (FIGS. 8a-8b, 5c).

The modular osseointegrable and osseoinductive component in the scapular portion therefore comprises a glenoid base-plate 17 and a concave glenoid insert 16 both having an asymmetric, pear-shaped anatomical shape, with a front profile different from the rear profile and a different upper profile with respect to the lower profile which determines a version for the right side and a version for the left side of the user's body. The glenoid base-plate 17 and the modular anatomical glenoid insert 16, in fact, having the same form and size, have a version for the right side and a version for the left side of the patient's body.

Figure 1:
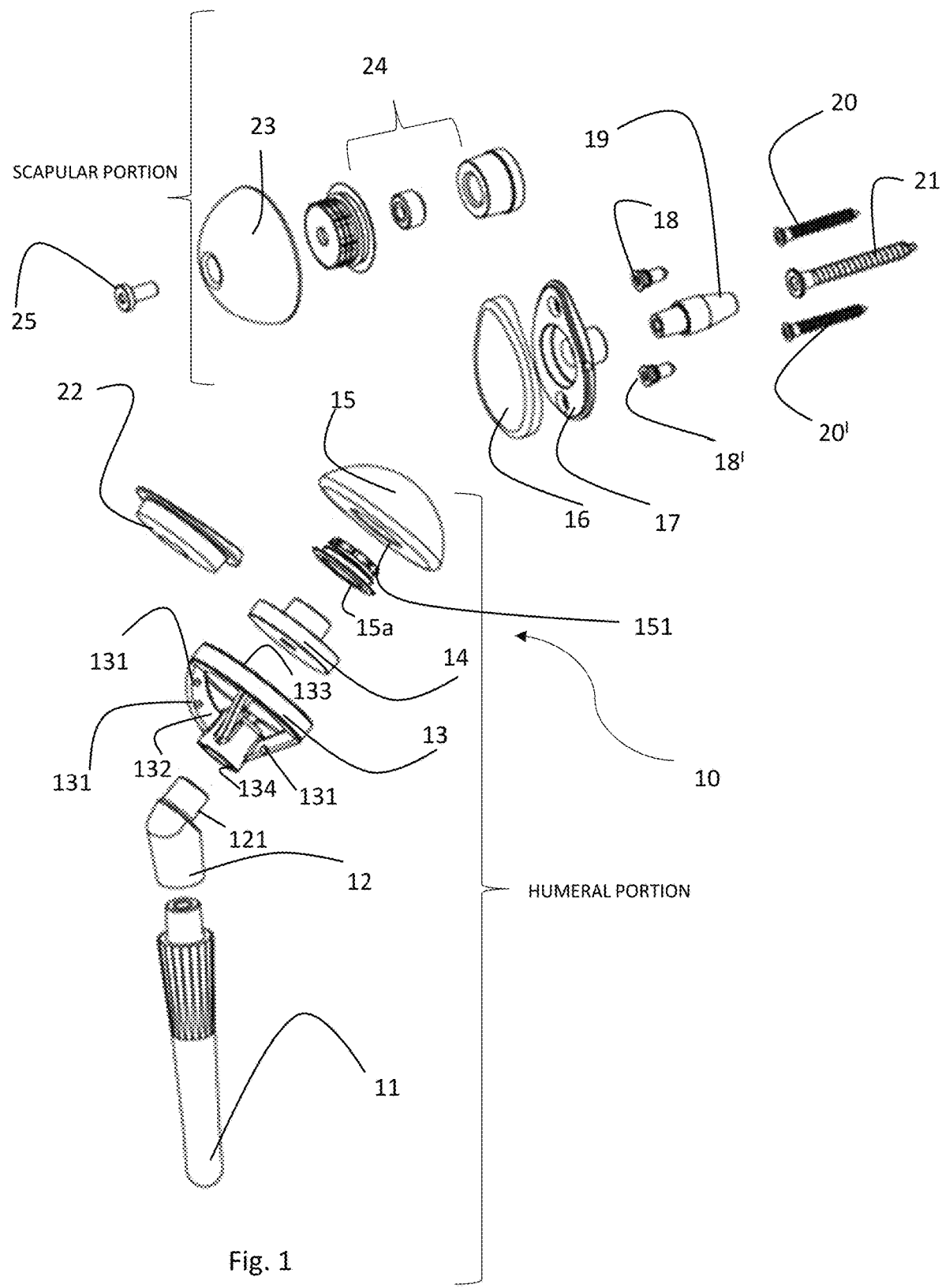
FIG. 1 is an exploded perspective view illustrating the total shoulder prosthesis system made according to the invention.

As illustrated in FIG. 1, the glenoid base-plate 17 is fixed to the glenoid bone without the use of cement but through a pair of lower and upper pivot screws 18, 18I, and through a central pin 19, made of titanium alloy powder Ti6Al4V (ASTM F3001/14), with the SLM technology with titanium trabeculation.

Advantageously, the pin 19 is coupled in a hole provided on the glenoid base-plate 17 by means of a morse cone coupling.

Figure 7D:
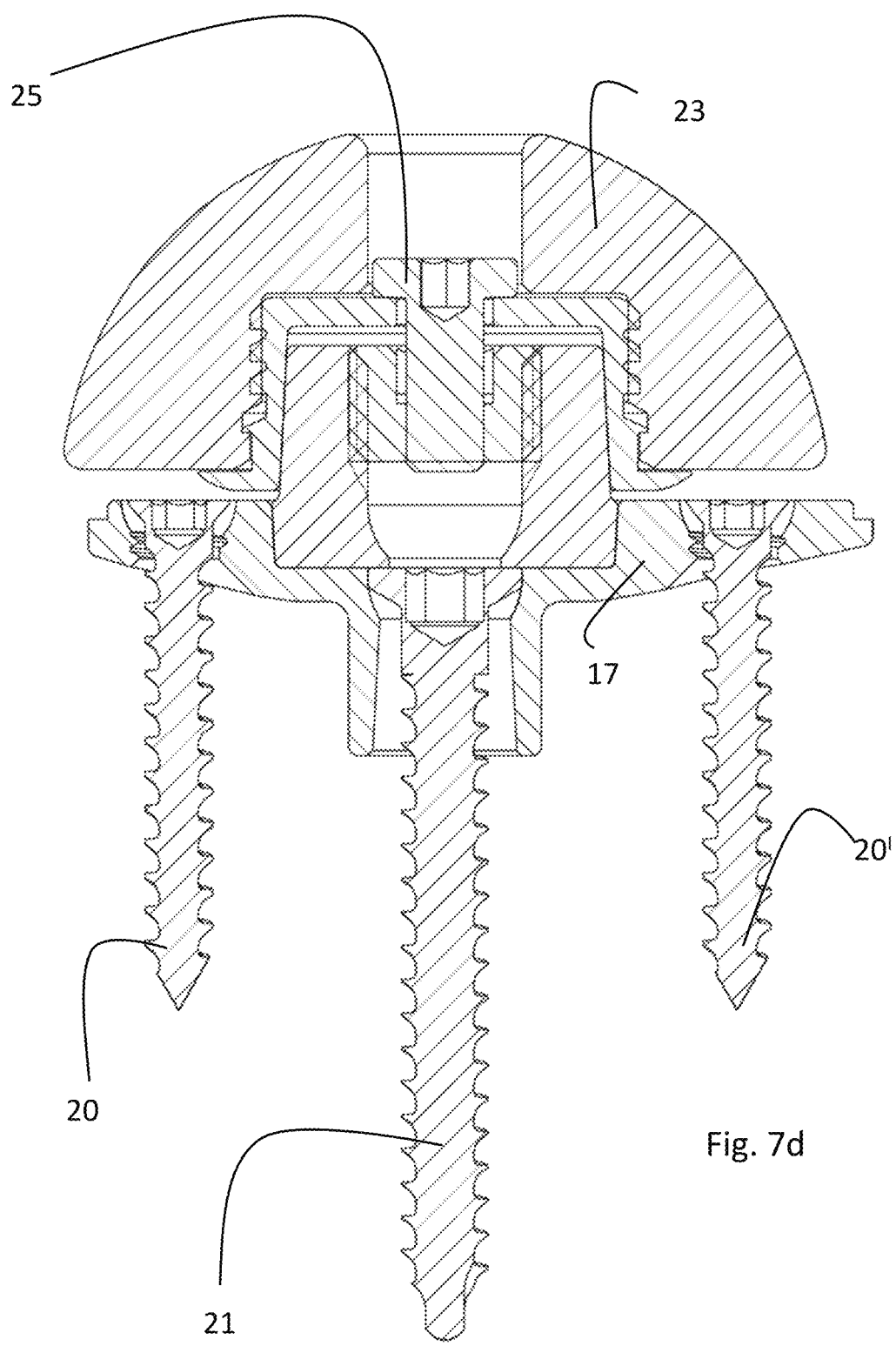
FIG. 7d is a section showing the glenoid component with glenosphere, a short safety screw, adapter, central fixing screw and lower and upper fixing screws.

Alternatively to or in combination with said screws 18, 18I and said pin 19, as shown in FIG. 7d, threaded screws 20, 20I and/or a threaded central fixing screw and bicortical in compression 21, can be provided.

According to the present invention, in the case of the production of a reverse prosthesis, as illustrated in FIGS. 3, 6, 7a-7c:

the components 14, 15a and 15, i.e. the adapter for the humeral head 14, the anatomical humeral head in polyethylene 15 and the ring for the morse cone 15a provided in the humeral portion of the prosthesis 10, are replaced by a concave insert for the reverse prosthesis 22, i.e. an articular component made of metallic material with an articulation surface with glenosphere 23, which is concave spherical with one radius.

Said concave insert 22 is coupled with the proximal base 133 of the humeral body 13 by means of a morse cone coupling.

Said humeral insert for a reverse prosthesis 22 can be provided in different sizes, with different CCD angles and with different thicknesses.

Advantageously, it is made of titanium alloy Ti6Al4V (ISO 5832/3) coated with TiNbN with the PVD technology (Physical Vapour Deposition) to make it tribologically compatible in articulation with the glenosphere in UHMWPE.

The anatomical glenoid insert 16 with a concave surface is substituted by a glenosphere for a reverse prosthesis 23, i.e. an articular component made of a plastic material such as polyethylene with a convex spherical articular surface with one radius, which can be fixed to the glenoid base plate 17 through an adapter for the glenosphere 24 and a fixing screw 25, for example made of titanium alloy Ti6Al4V (ISO 5832/3).

The glenosphere for a reverse prosthesis 23 is advantageously made of ultra high molecular weight polyethylene.

It can be made, for example, of UHMWPE or UHMWPE stabilized with vitamin E.

As shown in FIGS. 7a, 7c and 7d, the glenosphere 23 is attached to the base glenoid 17 again using the glenosphere adapter 24.

In the case of using a central peg, a long fixing screw for the glenosphere is used for fixing the glenosphere 23, whereas when using the central fixing screw instead of the peg, a short fixing screw must be used for the glenosphere and its relative threaded grub screw inside the adapter 24.

The shoulder prosthesis of the present invention is therefore a modular prosthetic system for total shoulder arthroplasty and total reverse shoulder arthroplasty.

It is in fact possible to convert from an anatomical prosthesis to a reverse prosthesis replacing only the articular components without replacing the components implanted in the humeral and scapular bone.

Furthermore, the modularity of said prosthesis allows the passage from a stemless implant for a first implant to a stemmed implant, intraoperatively and with the same humeral component 13.

Unlike the prior art in which the prosthetic humeral head is spherical with one radius, the prosthetic humeral head 15 in the anatomical prosthesis, object of the present invention, is elliptical with an elliptical base section with two diameters, thus respecting the anatomy of the humeral head. Furthermore, said prosthetic head 15 is made, for an anatomical prosthesis, in UHMWPE or UHMWPE with vitamin E.

The anatomical glenoid insert 16 is advantageously also made of TiNbN-coated titanium alloy with a two-radius surface: a radius of the anterior-posterior profile and a radius of the inferior-superior profile; it also has an asymmetrical, pear-shaped anatomical form, respecting the anatomy of the glenoid.

Similarly, the glenoid base-plate 17 has an asymmetrical pear-shaped anatomical form, respecting the anatomy of the glenoid.

It can be advantageously produced with the SLM technology characterized by a trabecular structure, highly porous, in titanium alloy (Traser®).

For a greater anatomical adaptability of the prosthesis, in the passage from stemless to stemmed implants, the metaphyseal humeral component 12 can have different offsets and CCD angles.

All of the components of the prosthesis are made of materials without the most common allergenic elements, such as nickel, cobalt, chrome, molybdenum.

Figure 2:
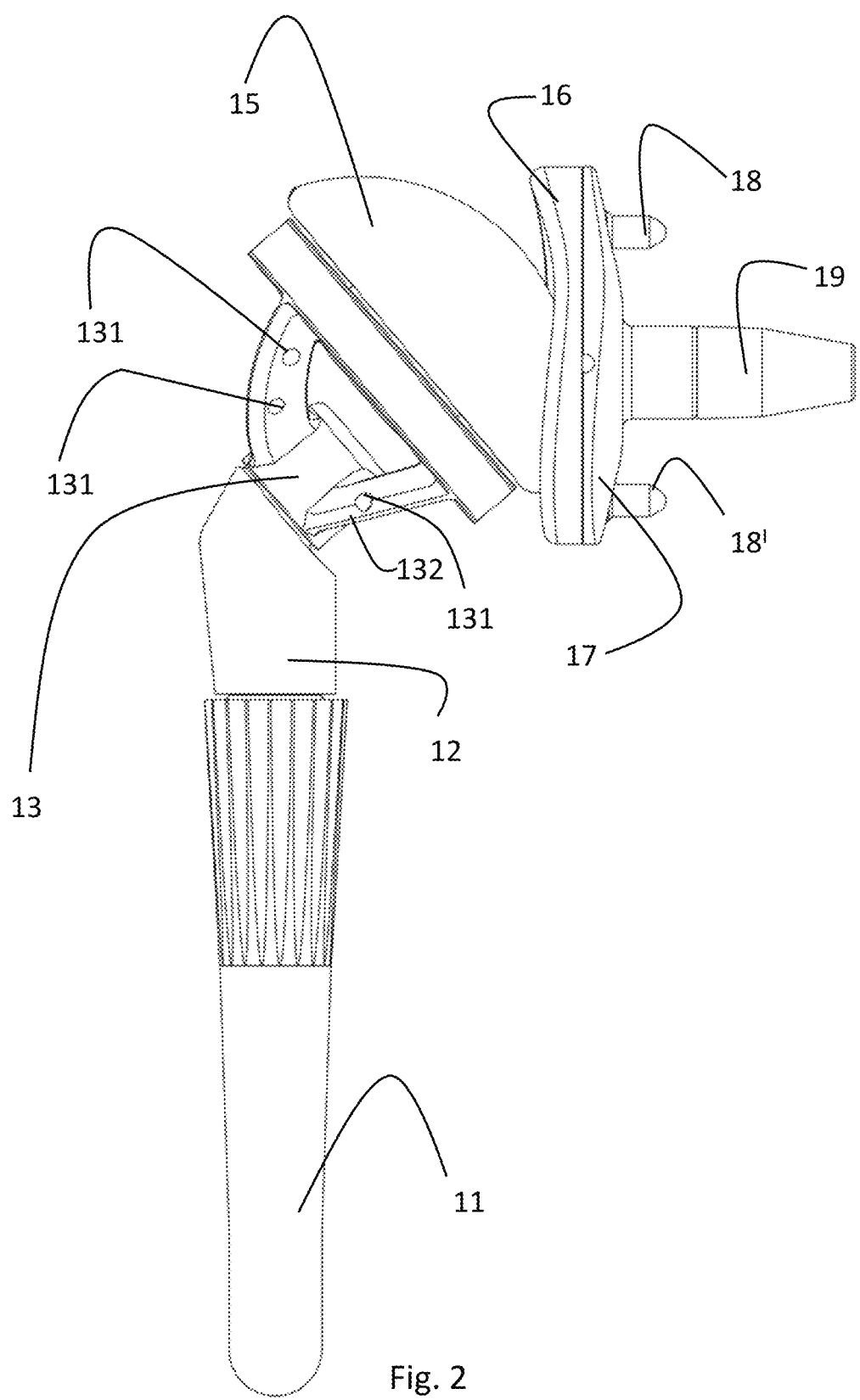
FIG. 2 is a raised view of the prosthesis of FIG. 1 in the stemmed anatomical configuration.

FIG. 2 shows an overall view of the humeral portion and the scapular portion in the anatomical configuration with a humeral stem 11 (so-called stemmed configuration): with reference to the humeral portion, the humeral head 15 made of polyethylene is coupled with the humeral body 13, by means of the humeral head adapter 14 and the ring of the morse cone 15a. The corresponding scapular portion provides the glenoid base-plate 17 (metal-back) fixed by screws 20, 20I, 21 and/or pins 18, 18I, 19 to the scapular bone and above which the metal anatomical glenoid insert 16 is assembled.

Figure 4:
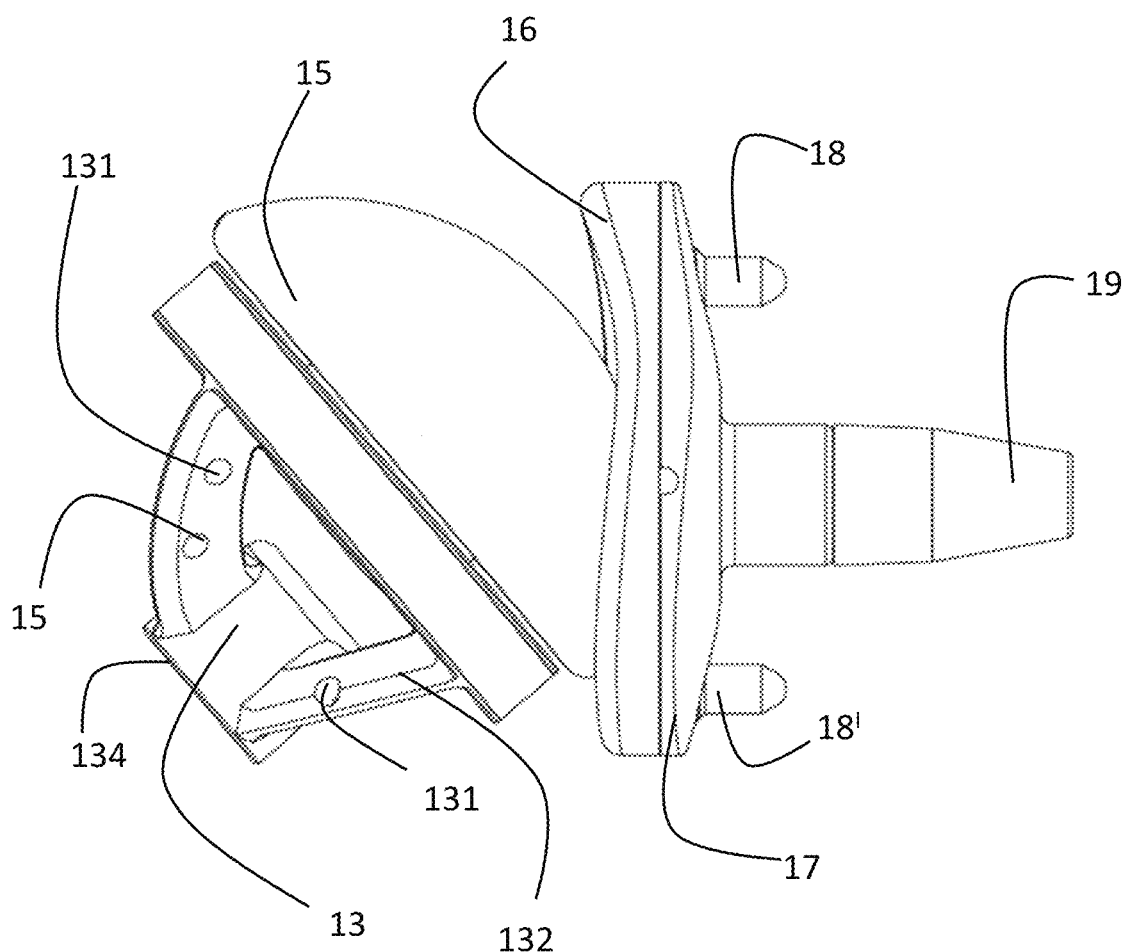
FIG. 4 is an overall view of the prosthesis according to the invention, but in the stemless anatomical configuration.

Analogously to FIG. 2, FIG. 4 shows an overall view of the humeral portion and the scapular portion in the anatomical configuration but without the humeral stem 11 (so-called stemless configuration).

FIGS. 5a, 5b and 5c how a sectional view of the portions of the humeral component 13, 14, 15a, 15 and scapular portions 16, 17, 18, 18I, 19 coupled together in the stemless anatomical configuration.

Figure 3:
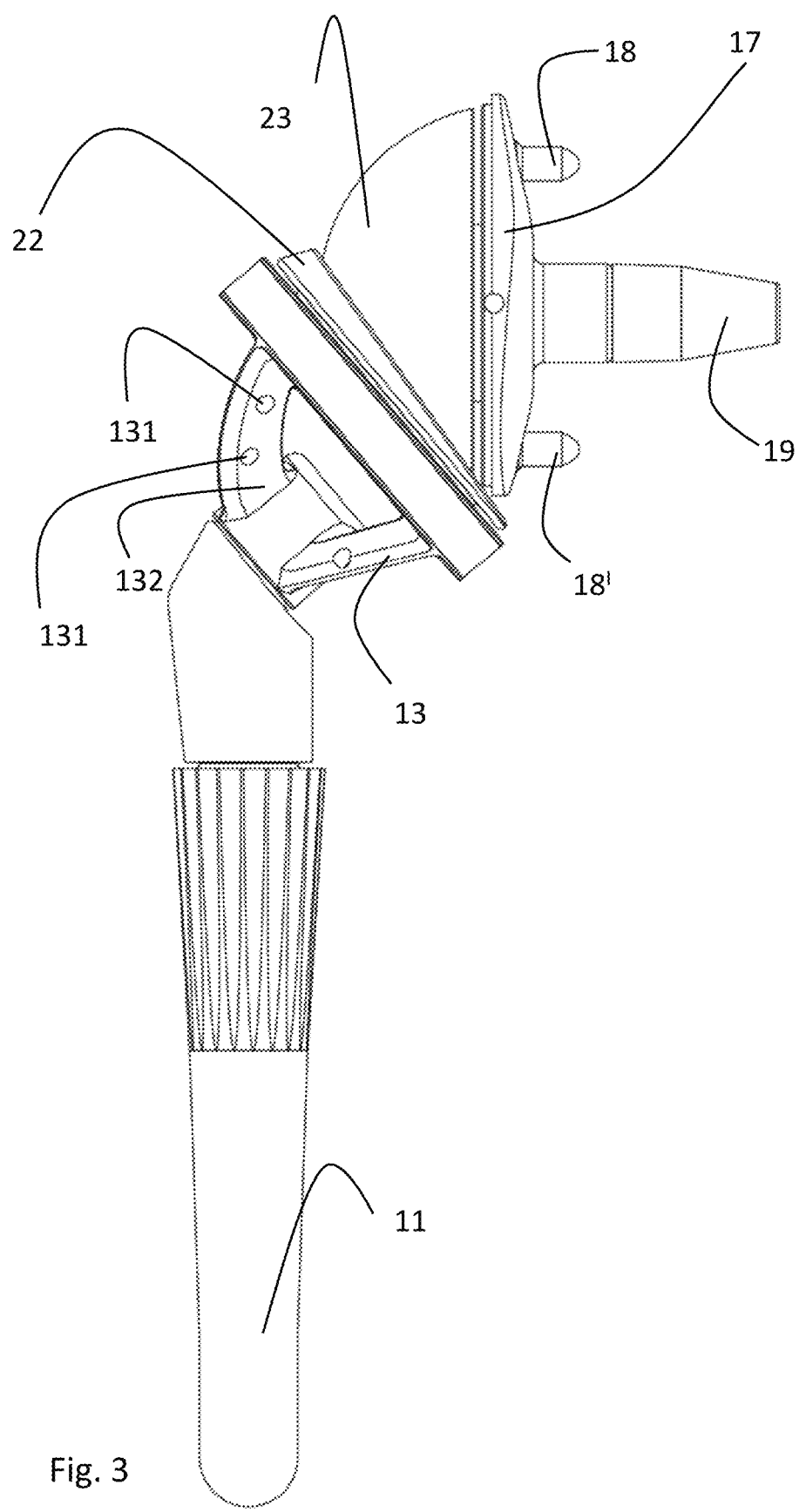
FIG. 3 is a view similar to FIG. 2, but showing the prosthesis in the reverse configuration.

FIG. 3 illustrates an overall view of the humeral portion and the scapular portion in the reverse configuration with a humeral stem 11 (so-called stemmed configuration): with reference to the humeral portion, the metal humeral insert 22 with a concave spherical surface with one radius is coupled with the humeral body 13. The corresponding scapular portion provides the glenoid base-plate 17 (metal-back) fixed to the bone by screws 20,20I, 21 and/or pins 18, 18I, 19 and on which the glenosphere 23 in UHMWPE or UHMWPE with vitamin E, is assembled.

Figure 6:
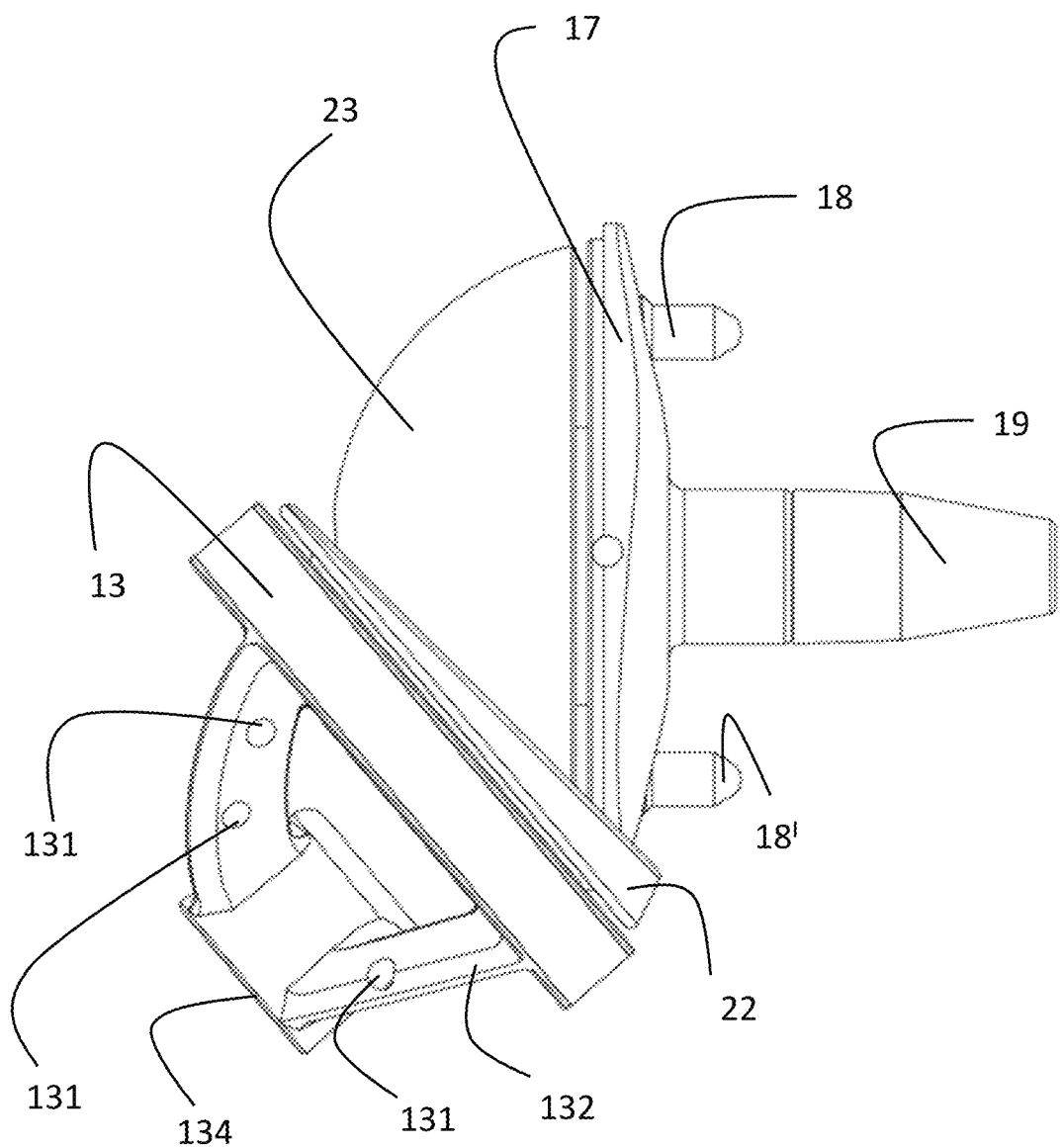
FIG. 6 is an overall view of the prosthesis according to the invention, but in the stemless reverse configuration.

Analogously to FIG. 3, FIG. 6 illustrates an overall view of the humeral portion and the scapular portion in the reverse configuration but without the humeral stem 11 (so-called stemless configuration). FIGS. 7a, 7b and 7c show a sectional view of the portions of the humeral component 13,22 and scapular portions 23,17,18, 18I, 19 coupled together in the reverse configuration without a stem 11 (stemless).

FIG. 7d shows an embodiment with a glenoid component with central, lower and upper fixing screws.

The prosthesis object of the present invention is destined for substituting the scapular glenoid and the humeral head in total shoulder arthroplasty for the first implant and revision or of the humeral head alone in the shoulder endoprosthesis.

The components are destined for being implanted by biological fixation (press-fit technique without using bone cement) and using bone cement (only monoblock glenoid and cemented stems).

The prosthesis system can therefore comprise the following types of components:

| | Prosthetic component | Description |
|---|---|---|
| 11 | Humeral stem | Humeral stem for the stemmed prosthetic configuration. Its function is to anchor the humeral core component to the humeral diaphysis. Available in the versions for first implant or revision by both biological fixation (press-fit) and cement fixation |
| 12 | Metaphyseal humeral connector | Component through which the humeral stem is fixed to the humeral core. It allows passage from the stemless prosthetic configuration to the stemmed configuration. |
| 13 | Humeral body or humeral core | This represents the stemless humeral component which can be used both in the anatomical configuration and in the reverse configuration and allows passage intraoperatively from a stemless configuration to a stemmed configuration. The fixation method is through press-fit without bone cement . . . |
| 14 | Adapter for anatomical humeral head | Component used for mounting the anatomical humeral head on the humeral core. |
| 15 | Anatomical humeral head | Articular component used for the anatomical configuration only. In the version for total prosthesis it is made of a plastic material and is characterized by an elliptical convex surface for coupling with the glenoid insert. |
| 16 | Anatomical glenoid insert | Glenoid articular component used in the anatomical prosthetic configuration only. It is characterized by an asymmetrical anatomical form of the glenoid and by a 2-radius concave articular surface for the coupling with the head. It is mounted above the glenoid base-plate. It is coated with TiNbN. |
| 17 | Glenoid base-plate | Metal component for anchorage to the glenoid bone characterized by an asymmetrical anatomical form. In the anatomical prosthesis configuration, the component is mounted with the anatomical glenoid insert. In the reverse configuration, it is mounted with the glenosphere. |

-continued

| | Prosthetic component | Description |
|---|---|---|
| | | Available in two versions, the first with titanium trabeculae, the second with HA coating. The fixing mode is through press-fit without bone cement |
| 18, 18' | Screw-pin Glenoid base-plate | Pre-assembled component in the lower and upper holes of the glenoid base-plate |
| 19 | Central Peg for glenoid base-plate | Component to be enconed on the glenoid base-plate for anchorage to the glenoid bone without the use of cement. The surface in contact with the bone is characterized by a titanium trabeculation. |
| 20, 20' | Fixing screw Glenoid base-plate | Cortical screws to be used in substitution of the pin-screws of the glenoid base-plate. |
| 21 | Central glenoid base-plate fixing screw | Bicortical compression screw to be used as an alternative to the central peg of the glenoid base-plate. |
| 22 | Humeral insert for reverse prosthesis | Metal articular component used in the reverse prosthesis configuration. It is characterized by a concave spherical articular surface which articulates with the glenosphere. |
| 23 | Glenosphere for reverse prosthesis | Polyethylene articular component used only for the reverse prosthesis configuration. |
| 24 | Glenosphere adapter | Component used for mounting the glenosphere on the glenoid base-plate. |
| 25 | Safety screws for glenosphere | Screw for fixing the glenosphere to the glenoid plate-base |

The materials which can be used are the following:

| ID | Prosthetic component | Material | Applicable standards |
|---|---|---|---|
| 11 | Non-cemented humeral stem | Ti6Al4V, hydroxyapatite | ISO 5832/3, ISO 13779 |
| 11 | Cemented humeral stem | Ti6Al4V | ISO 5832/3 |
| 12 | Metaphyseal humeral connector | Ti6Al4V | ASTM F 3001-14 |
| 13 | Stemless humeral Core | Ti6Al4V | ASTM F 3001-14 |
| 14 | Adapter for anatomical humeral head | Ti6Al4V | ISO 5832/3 |
| 15 | Anatomical humeral head | UHMWPE UHMWPE + 0.1% wt Vitamin E Ti6Al4V | ISO 5834/1/2$^{1/2}$, ASTM F 2695-12 ISO 5832/3 |
| 16 | Anatomical glenoid insertion | Ti6Al4V, TiNbN | ISO 5832/3 |
| 17 | Glenoid base-plate | Ti6Al4V | ASTM F 3001-14 |
| 18, 18' | Screw-pin | Ti6Al4V | ASTM F 3001-14 |
| 19 | Central peg for glenoid base-plate | Ti6Al4V | ASTM F 3001-14 |
| 20, 20' | Fixing screw for glenoid base-plate | Ti6Al4V | ISO 5832/3 |
| 21 | Central fixing screw for glenoid base-plate | Ti6Al4V | ISO 5832/3 |
| 22 | Humeral insert for reverse prosthesis | Ti6Al4V, TiNbN | ISO 5832/3 |
| 23 | Glenosphere | UHMWPE UHMWPE + 0.1% wt Vitamin E Ti6Al4V | ISO 5834/1/2, ASTM F2695-12 ISO 5832/3 |
| 24 | Safety screw for glenosphere | Ti6Al4V | ISO 5832/3 |
| 25 | Glenosphere adapter | Ti6Al4V | ISO 5832/3 |

The inversion of the materials of the articular components in the anatomical and reverse configuration (for example anatomical humeral head and glenosphere in UHMWPE with the addition of vitamin E, glenoid insert and humeral insert in titanium alloy TiNAl4V coated via PVD with TiNBN) allows the glenoid insert (compared to the conventional one in polyethylene) to be produced with a lower thickness, reducing the risk of over-stuffing the shoulder, as it is made of metal.

The elimination of the CrCo and steel alloys from the articulation materials in favour of UHMWPE and the alloy Ti&Al4V allows a lower weight of the prosthetic components.

The elimination of the CrCO and steel alloys from the materials makes the prosthesis, object of the present invention, free of cobalt, nickel, chromium and therefore hypoallergenic.

The prosthesis of the present invention is destined for the total substitution, both anatomical and reverse or partial, of the glenohumeral joint. The use of a stemmed or stemless configuration depends on the quality of the bone (previous surgeries, pseudoarthrosis, osteoporosis, bone defects etc.) of the epi-metaphyseal portion of the humerus.

The indications for use are:

Primary non-inflammatory degenerative joint diseases;

Secondary arthritis due to post-traumatic degenerative factors or degenerative rotator cuff diseases;

Avascular necrosis of the humeral head;

Joint degeneration secondary to rheumatoid arthritis, psoriatic arthritis or similar pathologies;

Acute fractures of the humeral head or glenoid;

Failure results of previous prosthetic interventions or osteosynthesis of the glenohumeral compartment.

In particular, the prosthesis, object of the present invention, is particularly suitable for total shoulder arthroplasty surgery in the case of:

arthritis of the glenohumeral joint;
necrosis of the humeral head;
rheumatoid arthritis;

and for total reverse shoulder prosthesis operations in the case of:

arthritis of the glenohumeral joint associated with rotator cuff arthropathy;
massive breakage of the rotator cuff;
outcomes of severe fractures of the proximal humerus;
revision of total or partial shoulder arthroplasty.

The results obtained from in vitro biocompatibility tests and from mechanical tests have demonstrated the high performances, safety and reliability of the prosthesis object of the present invention.

The prosthesis object of the invention therefore provides an anatomical configuration and a reverse configuration, for both the first implant and revision, with (stemmed) or without (stemless) a humeral stem.

The specific feature is its modularity that allows the passage from one configuration to another by adding and/or replacing the appropriate components thanks to their modularity.

The typical configurations with which it can be used are:

| ID | Prosthesis component | Total anatomical stemless | Total anatomical stemmed | Total reverse stemless | Total reverse stemmed |
|---|---|---|---|---|---|
| 11 | Humeral stem | | x | | x |
| 12 | Metaphyseal central connector | | x | | x |
| 13 | Humeral core | x | x | x | x |
| 14 | Adapter for anatomical humeral head | x | x | | |
| 15 | Anatomical humeral head | x | x | | |
| 16 | Anatomical glenoid insert | x | x | | |
| 17 | Glenoid base-plate | x | x | x | x |
| 18, 18ᴵ | Screw-pin for glenoid base-plate | x | x | x | x |
| 19 | Central Peg for glenoid base-plate | x | x | x | x |
| 20, 20ᴵ | Fixing screw for glenoid base-plate | x | x | x | x |
| 21 | Central fixing screw for glenoid base-plate | x | x | x | x |
| 22 | Humeral insert for reverse prosthesis | | | x | x |
| 23 | Glenosphere | | | x | x |
| 24 | Glenosphere adapter | | | x | x |
| 25 | Safety screw for glenosphere | | | x | x |

The anatomical version (replacement of the humeral and glenoid part) is particularly suitable in the case of:

Concentric arthrosis of the glenohumeral joint with a complete and functioning rotary cuff;

Necrosis of the humeral head; Necrosis of the glenoid;

Aseptic arthritis (A. rheumatoid, A. psoriatica); in the case of a complete rotary cuff.

The reverse version is particularly suitable in the case of:

Arthritis of the glenohumeral joint on extensive breakage of the rotational cuff (cuff arthropathy, disabling shoulder);

Massive irreparable breakage of the rotator cuff;

Outcomes of severe fractures of the non-reconstructable proximal humerus with a total anatomical prosthesis;

Revision of total or partial shoulder arthroplasty.

The suitability for the stemless or stemmed version (anatomical or reverse) depends on the epi-metaphyseal bone quality, in addition to the humeral diaphyseal morphology or possible presence of osteosynthesis means.

In order to obtain good osseointegration, an adequate quantity and quality of the bone is necessary for any stemless humeral implant. In the case of osteoporotic bone and/or general metabolic diseases relating to bone quality, the use of the stemmed version is recommended.

The objective mentioned in the preamble of the description of producing a prosthesis which is both very economical and functional, comprising all the advantages of the known art, but eliminating its drawbacks, has thus been achieved.

The protection scope of the invention is defined by the following claims.

The invention claimed is:

1. A total shoulder prosthesis comprising:

a humeral portion; and a scapular portion, the humeral portion and the scapular portion being each provided with an osseointegrable component and an articular component, wherein:

said osseointegrable component in the humeral portion comprises a humeral body shaped as a hemispherical asymmetrical cage having a proximal circular ring base facing the scapular portion, in a mounted condition of the shoulder prosthesis, and a distal cylindrical base, which has a longitudinal axis that is offset from a longitudinal axis of the proximal circular ring base and which is disposed to be on a transverse plane to the longitudinal axis of the proximal circular ring base and to be opposite with respect said proximal circular ring base, said proximal circular ring base and said distal cylindrical base being connected to each other by a plurality of arms, of the arms of said humeral body has one or more holes for favoring growth of humeral bone tissue and facilitating an anchorage of the humeral body to a bone, said proximal circular ring base being configured to be interchangeably coupled with a first articular component for an anatomical prosthesis or a concave insert for a reverse prosthesis, and said osseointegrable component in the scapular portion comprises a glenoid base-plate with an asymmetric anatomical form for coupling a second articular component for an anatomical prosthesis or a glenosphere for a reverse prosthesis, said first and said second articular components for anatomical prostheses or said concave insert and said glenosphere for reverse prostheses being intercoupled with each other in an operating condition.

2. The prosthesis according to claim 1, wherein said osseointegrable component in the humeral portion comprises a metaphyseal humeral connector for a morse cone coupling of the distal cylindrical base to a stem fixed inside a humeral bone.

3. The prosthesis according to claim 1, wherein at least the humeral body has, at least on an outer annular side of the proximal circular ring base, a structure with isotropically and irregularly oriented trabeculae, which is highly porous for favoring the anchorage, by press-fit, of the humeral body by pressure interlocking with the bone of a humeral metaphysis and for favoring a secondary biological anchorage through osseoinductivity and osseointegrability.

4. The prosthesis according to claim 1, wherein the plurality of arms consists of a first and a second pair of arms, a first pair having the arms of a smaller size and length than the arms of the second pair, said first pair being configured to be inserted in a bone portion of a humeral neck and said second pair being configured to be inserted in a bone portion of a greater tubercle, the prosthesis being configured to be inserted in a humerus in order to confer greater rotational stability to said humeral body and greater support on a humeral metaphyseal bone, thereby avoiding a distal migration of the humeral body downwards.

5. The prosthesis according to claim 4, wherein the first pair of arms is positioned on a lateral side of the distal cylindrical base, and wherein the second pair of arms having a smaller size and length is positioned on a medial side of the distal cylindrical base according to a direction described by an axis perpendicular to an axis in an anterior-posterior direction passing through a center of the distal cylindrical base.

6. The prosthesis according to claim 1, wherein the proximal circular ring base and the distal cylindrical base, are connected to each other by a first and a second pairs of the arms, the first pair being asymmetric with respect to the second pair with respect to an axis Y in an anterior-posterior direction passing through a center of the distal cylindrical base.

7. The prosthesis according to claim 1, wherein said glenoid base-plate and said concave glenoid insert have an anatomical, pear-shaped asymmetric form with a front profile different from a rear profile and an upper profile different from a lower profile.

8. The prosthesis according to claim 1, wherein said concave insert for the reverse prosthesis has an articulation surface with the glenosphere, said articulation surface of said concave insert having a single radius of curvature.

9. The prosthesis according to claim 1, wherein said glenosphere for the reverse prosthesis has an articulation surface with said concave insert, said articulation surface of said glenosphere being convex with a single radius of curvature.

10. The prosthesis according to claim 1, wherein said concave insert for the reverse prosthesis is made of a metallic material and said glenosphere for the reverse prosthesis is made of a plastic material.

11. The prosthesis according to claim 1, wherein said concave insert for the reverse prosthesis is made of titanium alloy Ti6A14V with a coating of TiNbN and said glenosphere for the reverse prosthesis is made of UHMWPE or UHMWPE with vitamin E.

12. The prosthesis according to claim 1, wherein said humeral body and said glenoid base-plate are made of a metallic material.

13. The prosthesis according to claim 1, wherein said concave insert is coupled with the proximal base of said humeral body by a morse cone coupling.

14. The prosthesis according to claim 1, wherein said glenosphere is coupled with said glenoid base-plate by one or more fixing means.

15. The prosthesis according to claim 1, wherein said glenoid base-plate is configured to be fixed to a scapular bone by means of one or more screws and/or pins.

* * * * *